United States Patent
Yamate et al.

(10) Patent No.: US 7,875,412 B2
(45) Date of Patent: Jan. 25, 2011

(54) POSITIVE ELECTRIFIED CHARGE CONTROL AGENT AND POSITIVE ELECTRIFIED TONER FOR DEVELOPING ELECTROSTATIC IMAGE

(75) Inventors: Osamu Yamate, Neyagawa (JP); Masashi Yasumatsu, Neyagawa (JP)

(73) Assignee: Orient Chemical Industries, Ltd., Osaka (JP)

( * ) Notice: Subject to any disclaimer, the term of this patent is extended or adjusted under 35 U.S.C. 154(b) by 967 days.

(21) Appl. No.: 11/730,446

(22) Filed: Apr. 2, 2007

(65) Prior Publication Data
US 2007/0231726 A1  Oct. 4, 2007

(30) Foreign Application Priority Data
Apr. 3, 2006 (JP) ............................. 2006-102410

(51) Int. Cl.
*G03G 9/097* (2006.01)
(52) U.S. Cl. ............ 430/108.3; 430/108.1; 430/108.24; 430/123.41; 549/4; 549/214; 556/406; 556/408
(58) Field of Classification Search ............... 430/108.3, 430/108.1, 123.41, 108.24; 549/4, 214; 556/406, 556/408
See application file for complete search history.

(56) References Cited

U.S. PATENT DOCUMENTS

| 5,545,502 | A | * | 8/1996 | Ono et al. ................. | 430/108.2 |
| 2006/0172210 | A1 | | 8/2006 | Yamate et al. ............ | 430/108.3 |
| 2007/0037083 | A1 | | 2/2007 | Yamate et al. ............ | 430/108.3 |

FOREIGN PATENT DOCUMENTS

JP  62-062369  3/1987

(Continued)

OTHER PUBLICATIONS

English translation of JP 2004-046142 published Feb. 2004.*

*Primary Examiner*—Christopher RoDee
*Assistant Examiner*—Peter L Vajda
(74) *Attorney, Agent, or Firm*—Steptoe & Johnson, LLP

(57) ABSTRACT

A positive electrified charge control agent comprising a silicon complex compound of an effective component represented by the following chemical formula (I) and/or chemical formula (II)

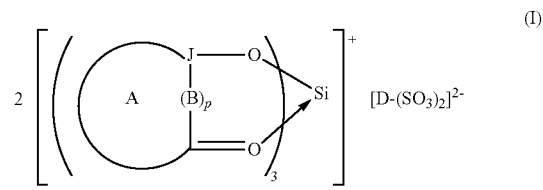

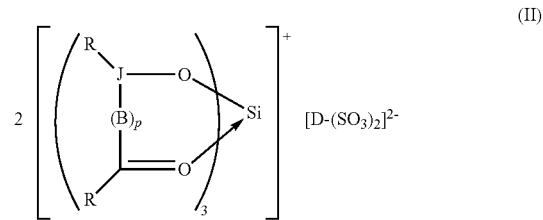

(in the formula (I) and formula (II), $[D-(SO_3)_2]^{2-}$ is a bivalent anion of an organic acid having at least two sulfonic acid groups, p is 0 or 1, B is a bonding line when p is 0, B is a carbon atom or a nitrogen atom when p is 1, J is a carbon atom or a nitrogen atom, A is an organic group which forms a ring with $(B)_p$ and J, both of R are same or different to each other and are an organic group, and these both of R are independent or form a heterocyclic ring). A positive electrified toner for developing an electrostatic image comprises the positive electrified charge control agent. A charge control method of the positive electrified toner for developing the electrostatic image comprises a step for making the toner positively electrified by friction.

14 Claims, 3 Drawing Sheets

FOREIGN PATENT DOCUMENTS

| | | |
|---|---|---|
| JP | 63-206768 | 8/1988 |
| JP | 03-276166 | 12/1991 |
| JP | 04-293057 | 10/1992 |
| JP | 2004-046142 * | 2/2004 |
| JP | 2004-143049 | 2/2004 |

* cited by examiner

POSITIVE ELECTRIFIED CHARGE CONTROL AGENT AND POSITIVE ELECTRIFIED TONER FOR DEVELOPING ELECTROSTATIC IMAGE

BACKGROUND OF THE INVENTION

This invention relates to a positive electrified charge control agent which is used for a positive electrified toner for developing an electrostatic image or a powder paint, a positive electrified toner for developing an electrostatic image including the agent, and a charge control method of the toner.

Electro photography applied to a copy machine, printer or facsimile performs to develop an electrostatic latent image on a photosensitive frame with toner having frictional electrification and then the imaged toner is transferred and fixed to copy or print onto paper.

The electrification property of the toner is an important factor to raise a development speed of electro photography and form the vivid image. Therefore, a charge control agent is added to the toner so as to control a proper quantity of the electrification stably and quicken a rise speed of the electrification. The charge control agent is for positive or negative electrification. For instance, as the positive electrified charge control agent, it is disclosed in Japanese Patent Provisional Publication Nos. 63-206768 and 62-62369. As the negative electrified charge control agent, it is disclosed in Japanese Patent Provisional Publication No. 3-276166. The charge control agents disclosed in those publications are organic metal complex compounds which organic ligands are coordinated to a central atom of metal such as aluminum, tin, lead, cobalt, iron, nickel, zinc, chromium, copper, barium, and beryllium. While the charge control agent for negative electrification disclosed in Japanese Patent Provisional Publication No. 4-293057 is compound which organic ligands are coordinated to organic ligand to a central atom of silicon. Therefore, the toner including this charge control agent for negative electrification is a negative electrified toner. The toner is used for developing a positive electrified electrostatic latent image on a photosensitive frame.

It is required that the toner has more excellent electrification property and stability than a prior toner to achieve high speed and high definition in copying and printing. Furthermore, it is required that the toner and the charge control agent included therein have preservation stability and environmental hygiene on the latest trend.

Moreover, it is required that the charge control agent is able to be used of a powder paint for a electrostatic powder paint method which attracts and bakes the electrified powder paint onto a surface of a frame work having charge, and has the proper electrification property and stability.

DISCLOSURE OF THE INVENTION

The present invention has been developed to solve the foregoing problems. It is an object of the present invention to provide a charge control agent which causes excellent positive electrification property of a positive electrified toner for developing an electrostatic image and a powder paint, and a positive electrified toner for developing an electrostatic image which includes the agent, has excellent electrification stability, preservation stability, environmental resistance and makes high definition of the developed image. It is another object of the present invention to provide a charge control method using the toner.

The positive electrified charge control agent of the present invention developed for accomplishing the foregoing objects, comprises a silicon complex compound of an effective component represented by the following chemical formula (I) and/or chemical formula (II)

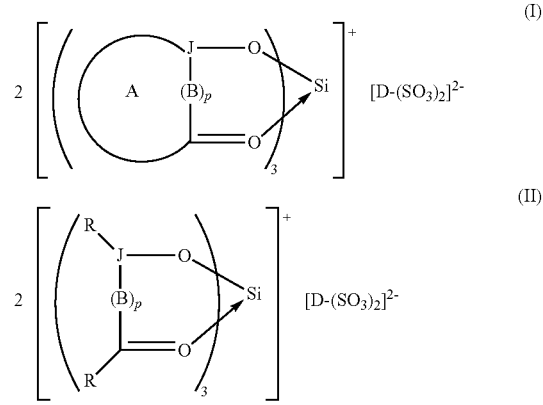

(in the formula (I) and formula (II), $[D\text{-}(SO_3)_2]^{2-}$ is a bivalent anion of an organic acid having at least two sulfonic acid groups, p is 0 or 1, B is a bonding line when p is 0, B is a carbon atom or a nitrogen atom when p is 1, J is a carbon atom or a nitrogen atom, A is an organic group which forms a ring with $(B)_p$ and J, both of R are same or different to each other and are an organic group, and these both of R are independent or form a heterocyclic ring).

In the positive electrified charge control agent, the group of

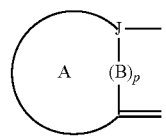

in the chemical formula (I) is preferably represented by the following chemical formula (III)

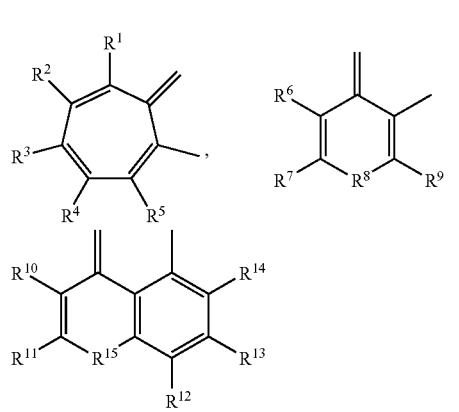

(in the chemical formula (III), $R^1$ to $R^7$ and $R^{10}$ to $R^{14}$ are same or different to each other and are selected from the group consisting of a hydrogen atom, a hydroxyl group, a hydroxyalkyl group, a carboxyl group, an alkoxycarbonyl group, a halogen atom, an alkyl group, an alkoxyl group, an acyl group, an alkenyl group, a nitro group, a cyano group, an amino group, an alicyclic group, an aralkyl group and an aryl group, or a group forming a saturated or unsaturated fused-ring of 3 to 7 carbons at positions of neighboring group; $R^8$ and $R^{15}$ are an oxygen atom, a carbonyl group, or an imino group; $R^9$ is selected from the group consisting of a hydrogen atom, a hydroxyl group, a hydroxyalkyl group, a carboxyl group, an alkoxycarbonyl group, a halogen atom, an alkyl group, an alkoxyl group, an acyl group, an alkenyl group, a nitro group, a cyano group, an amino group, an alicyclic group, an aralkyl group and an aryl group); and the group of

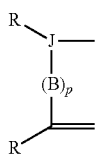

in the chemical formula (II) is preferably represented by the following chemical formula (IV)

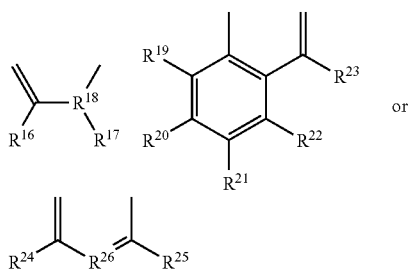

(IV)

(in the chemical formula (IV), $R^{16}$, $R^{17}$ and $R^{23}$ to $R^{25}$ are same or different to each other and are selected from the group consisting of a hydrogen atom, a hydroxyl group, a hydroxyalkyl group, a carboxyl group, an alkoxycarbonyl group, a halogen atom, an alkyl group, an alkoxyl group, an acyl group, an alkenyl group, a nitro group, a cyano group, an amino group, an alicyclic group, an aralkyl group and an aryl group; $R^{18}$ is a methine or a nitrogen atom; $R^{19}$ to $R^{22}$ are same or different to each other and are selected from the group consisting of a hydrogen atom, a hydroxyl group, a hydroxyalkyl group, a carboxyl group, an alkoxycarbonyl group, a halogen atom, an alkyl group, an alkoxyl group, an acyl group, an alkenyl group, a nitro group, a cyano group, an amino group, an alicyclic group, an aralkyl group and an aryl group, or a group forming a saturated or unsaturated fused-ring of 3 to 7 carbons at positions of neighboring group; $R^{26}$ is a nitrogen atom or a carbon atom having one or more substitutional groups such as an alkyl group having 1 to 8 carbons illustrated with methyl group, ethyl group, propyl group, butyl group, an alkoxyl group having 1 to 8 carbons illustrated with methoxyl group, ethoxyl group, propoxyl group, butoxyl group, an halogen atom of Cl, Br, I, F, an aryl group illustrated with phenyl group, tolyl group, naphthyl group, a hydrogen atom, or no substitutional group).

It is preferable that the silicon complex compound represented by the chemical formula (I) is a compound obtained by an ion-exchanging reaction of a silicon complex salt represented by the following chemical formula (V)

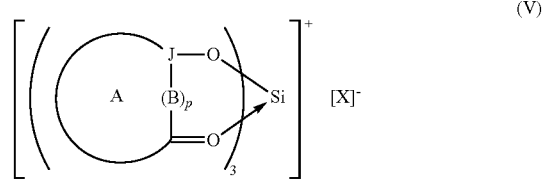

(in the chemical formula (V), X is a halogen atom; p, B, J and A are the same above) with an organic acid or a salt thereof, and the silicon complex compound represented by the chemical formula (II) is a compound obtained by an ion-exchanging reaction of a silicon complex salt represented by the following chemical formula (VI)

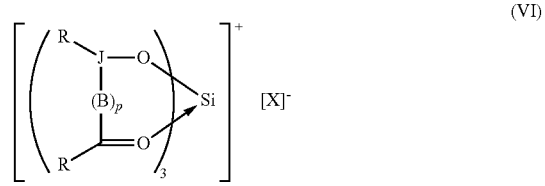

(in the chemical formula (VI), X is a halogen atom; p, B, J and R are the same above) with an organic acid or a salt thereof.

The content of allowable residual halogen in the silicon complex compound represented by the chemical formula (I) or the chemical formula (II) is preferably at most 0.2%.

The rate of weight-decrease of the silicon complex compound represented by the chemical formula (I) or the chemical formula (II) after heating for 2 hours under 180° C. is preferably at most 10.0%.

The volume resistivity of the silicon complex compound represented by the chemical formula (I) or the chemical formula (II) is preferably $1.0 \times 10^{13}$ to $5.0 \times 10^{15}$ Ω·cm.

The positive electrified toner for developing the electrostatic image comprises the above-mentioned positive electrified charge control agent.

The positive electrified toner for developing the electrostatic image comprises 0.1 to 10 parts by weight of the positive electrified charge control agent and 100 parts by weight of a resin for the toner.

The charge control method of the positive electrified toner for developing the electrostatic image comprises a step for making the above-mentioned toner positively electrified by friction.

The charge control agent comprising the silicon complex compound of the present invention accomplishes excellent positive electrification property of the positive electrified toner for developing the electrostatic image and the powder paint. Especially the charge control agent has an excellent heat resistance, an excellent preservation stability and an excellent environmental resistance. The charge control agent is added to not only monochrome toner but also various chromatic color toners extensively to be used.

The positive electrified toner for developing an electrostatic image comprising the charge control agent has a quick rise speed of the electrification, and has an excellent electrification stability for long period of time even if temperature and humidity change. There is very little variation of the electrification property between the obtained toner particles because the toner has an excellent heat stability and the charge control agent has an excellent dispersibility to the resin for the toner.

The positive electrified toner for developing an electrostatic image is suitable to develop the electrostatic image on the photosensitive frame made from any matter of regardless of organic or inorganic type. Furthermore, it is suitable to develop an electrostatic image on not only a regular paper but also a processing paper and a processing film. The toner image developed by the positive electrified toner for developing an electrostatic image has a fixing ability with an extensive range of temperature. The fixed images are vivid and no fogginess to back ground, and has non-offset property and no degradation for a long time.

MODE FOR CARRYING OUT THE INVENTION

Figure 1:
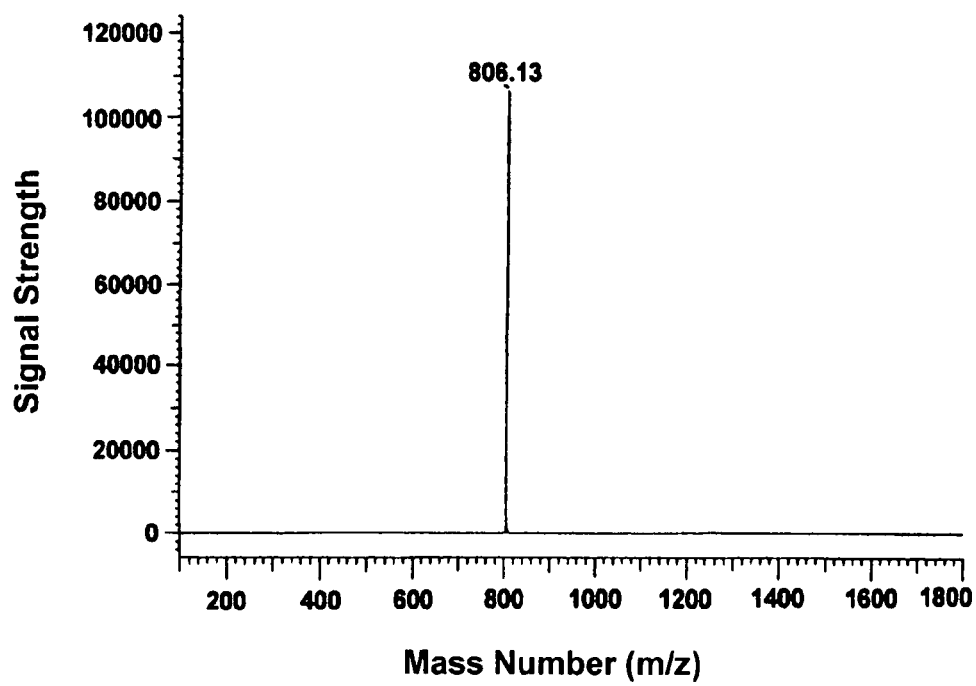
FIG. 1 is a figure showing a measurement result by a liquid chromatography mass spectrometric analysis of an intermediate of a silicon complex compound of Compound Example 1 comprised in a positive electrified charge control agent to which the present invention is applied.

Hereunder, embodiments of the present invention are explained in detail. However, the invention is not limited to these embodiments.

The positive electrified charge control agent of the present invention comprises a silicon complex compound of an effective component represented by the chemical formula (I) or the chemical formula (II). The silicon complex compound comprises a salt between a silicon complex cation and a bivalent anion of an organic acid having at least two sulfonic acid groups. It is preferable that the silicon complex compound has a group represented by the chemical formula (III) or the chemical formula (IV).

The silicon complex compound represented by the chemical formula (I) or the chemical formula (II) is obtained by an ion-exchanging reaction of a silicon complex salt represented by the chemical formula (V) or the chemical formula (VI) with an organic acid or a salt thereof.

In the chemical formula (III) or the chemical formula (IV), $R^1$ to $R^{26}$ are the same above. More concrete examples of $R^1$ to $R^7$, $R^9$ to $R^{14}$ and $R^{16}$ to $R^{25}$ are as follows.

Examples of a halogen atom are Cl, Br, I, F.

Examples of an alkyl group are an alkyl group having 1 to 18 carbons such as methyl group, ethyl group, propyl group, isopropyl group, butyl group, isobutyl group, tert-butyl group, pentyl group, hexyl group, heptyl group and octyl group. These alkyl groups may have one or more substitutional groups such as a nitro group, a halogen atom illustrated with Cl, Br, I and F, or an alkoxyl group having 1 to 18 carbons, or may have no substitutional group.

Examples of an alkoxyl group are an alkoxyl group having 1 to 18 carbons such as methoxyl group, ethoxyl group, propoxyl group, butoxyl group, pentyloxyl group and hexyloxyl group. These alkoxyl groups may have one or more substitutional groups such as a hydroxyl group, a nitro group, a halogen atom illustrated with Cl, Br, I and F, or an alkoxyl group having 1 to 18 carbons, or may have no substitutional group.

Examples of an acyl group are formyl group, acetyl group, propionyl group, butyryl group, valeryl group, pivaloyl group and benzoyl group.

Examples of a hydroxyalkyl group are hydroxymethyl group, hydroxyethyl group, hydroxypropyl group, hydroxybutyl group, hydroxypentyl group and hydroxyhexyl group.

Examples of an alkenyl group are vinyl group, allyl group, propenyl group and butenyl group.

Examples of an alkoxycarbonyl group are methoxycarbonyl group, ethoxycarbonyl group, propoxycarbonyl group, butoxycarbonyl group, pentyloxycarbonyl group and hexyloxycarbonyl group.

Examples of an aryl group are phenyl group, tolyl group, butylphenyl group, octylphenyl group and naphthyl group. These aryl groups may have one or more substitutional groups such as a hydroxyl group, a nitro group, a halogen atom illustrated with Cl, Br, I, F, an alkyl group having 1 to 18 carbons or an alkoxyl group having 1 to 18 carbons, or may have no substitutional group.

Examples of an alicyclic group are a cycloalkyl group having 3 to 7 carbons such as cyclopropenyl group, cyclobutyl group, cyclohexyl group and cycloheptyl group. These alicyclic groups may have one or more substitutional groups such as a hydroxyl group, a nitro group, a halogen atom illustrated with Cl, Br, I, F, an alkyl group having 1 to 18 carbons or an alkoxyl group having 1 to 18 carbons, or may have no substitutional group.

Examples of an aralkyl group are a benzyl group and an alpha,alpha'-dimethylbenzyl group. These aralkyl groups may have one or more substitutional groups such as a hydroxyl group, a nitro group, a halogen atom illustrated with Cl, Br, I, F, an alkyl group having 1 to 18 carbons or an alkoxyl group having 1 to 18 carbons, or may have no substitutional group.

Examples of a group forming a saturated or unsaturated fused-ring of 3 to 7 carbons at positions of neighboring group are cyclopropene ring, cyclopropane ring, cyclobutadiene ring, cyclobutane ring, cyclopentadiene ring, cyclopentane ring, cyclohexane ring, cycloheptatriene ring and benzene ring. These groups may have one or more substitutional groups, or may have no substitutional group. It is preferable that the group is a benzene ring. Examples of the substitutional group of the fused-ring are a hydroxyl group, a halogen atom, an alkyl group, an alkoxyl group, an acyl group, an aralkyl group, an alicyclic group and an alkenyl group.

In the chemical formula (I) or the chemical formula (II), $[D\text{-}(SO_3)_2]^{2-}$ is a bivalent anion obtained from an organic acid of polysulfonic acid having at least two sulfonic acid groups ($-SO_3M$ which M is a hydrogen atom, an alkali metal or an ammonium). Examples of the organic acid are an aromatic organic acid having at least two sulfonic acid groups as the substitutional group and a fatty organic acid having at least two sulfonic acid groups as the substitutional group. It is preferable that the organic acid is the aromatic organic acid having at least two sulfonic acid groups on a benzene ring or on a naphthalene ring.

It is preferable that the organic acid is a naphthalenedisulfonic acid derivative represented by the following chemical formula (VII).

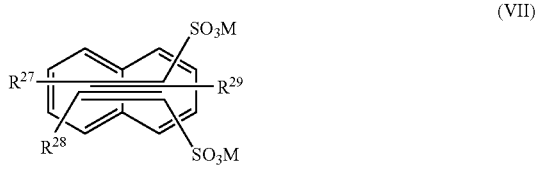

(VII)

(in the chemical formula (VII), M is a hydrogen atom, an alkali metal, an ammonium; $R^{27}$ to $R^{29}$ is a hydrogen atom, a hydroxyl group, an amino group, an alkylamino group such as methylamino group, ethylamino group, propylamino group, butylamino group, pentylamino group, hexylamino group, heptylamino group, octylamino group, an acetylamino group, a benzoylamino group, a nitro group, an alkyl group such as an alkyl group having 1 to 18 carbons illustrated with methyl group, ethyl group, propyl group, isopropyl group, butyl group, isobutyl group, tert-butyl group, pentyl group, hexyl group, heptyl group and octyl group, an alkoxyl group such as an alkoxyl group having 1 to 18 carbons illustrated with methoxyl group, ethoxyl group, propoxyl group, butoxyl group, pentyloxyl group and hexyloxyl group, an acetyloxyl group, a halogen atom such as Cl, Br, I and F, a phenyloxyl group, a carboxyl group, an acyl group such as formyl group, acetyl group, propionyl group, butyryl group, valeryl group, pivaloyl group and benzoyl group.

More concrete example of the organic acid is a naphthalene derivative represented by the following chemical formula (VIII). $R^{30}$ to $R^{37}$ are groups shown in Table 1.

TABLE 1

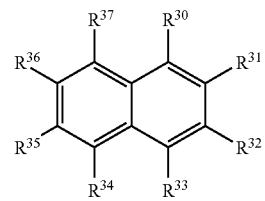

(VIII)

| Position of Sulfonic acid group | $R^{30}$ | $R^{31}$ | $R^{32}$ | $R^{33}$ | $R^{34}$ | $R^{35}$ | $R^{36}$ | $R^{37}$ |
|---|---|---|---|---|---|---|---|---|
| 1,2- Substitution Product | $SO_3M$ | $SO_3M$ | H | H | H | H | H | H |
| | $SO_3M$ | $SO_3M$ | H | OH | H | H | H | H |
| | $SO_3M$ | $SO_3M$ | H | H | H | H | $NH_2$ | H |
| 1,3- Substitution Product | $SO_3M$ | H | $SO_3M$ | H | H | H | H | H |
| | $SO_3M$ | H | $SO_3M$ | H | H | $NH_2$ | H | H |
| | $SO_3M$ | H | $SO_3M$ | H | $NH_2$ | $NH_2$ | H | H |
| | $SO_3M$ | H | $SO_3M$ | H | H | $NH(CH_3)$ | H | H |
| | $SO_3M$ | H | $SO_3M$ | H | H | H | OH | H |
| 1,4- Substitution Product | $SO_3M$ | H | H | $SO_3M$ | H | H | H | H |
| | $SO_3M$ | H | H | $SO_3M$ | OH | H | H | H |
| | $SO_3M$ | H | $NH_2$ | $SO_3M$ | H | H | H | H |
| | $SO_3M$ | H | H | $SO_3M$ | H | OH | H | H |
| 1,5- Substitution Product | $SO_3M$ | H | H | H | $SO_3M$ | H | H | H |
| | $SO_3M$ | H | H | $NHC=OCH_3$ | $SO_3M$ | H | OH | H |
| | $SO_3M$ | H | $NO_2$ | H | $SO_3M$ | H | H | H |
| | $SO_3M$ | H | $C(CH_3)_3$ | H | $SO_3M$ | H | $C(CH_3)_3$ | H |
| 1,6- Substitution Product | $SO_3M$ | H | H | H | H | $SO_3M$ | H | H |
| | $SO_3M$ | H | H | H | H | $SO_3M$ | H | $NO_2$ |
| | $SO_3M$ | H | H | H | OH | $SO_3M$ | H | H |
| | $SO_3M$ | H | H | $NH_2$ | H | $SO_3M$ | H | H |
| 1,7- Substitution Product | $SO_3M$ | H | H | H | H | H | $SO_3M$ | H |
| | $SO_3M$ | H | H | $NHC=OC_6H_5$ | OH | H | $SO_3M$ | H |
| | $SO_3M$ | H | H | $NHC=OCH_3$ | OH | H | $SO_3M$ | H |
| | $SO_3M$ | H | H | $NH_2$ | OH | H | $SO_3M$ | H |
| 1,8- Substitution Product | $SO_3M$ | H | H | H | H | H | H | $SO_3M$ |
| | $SO_3M$ | H | H | OH | H | H | H | $SO_3M$ |
| | $SO_3M$ | H | H | $CH(CH_3)_2$ | $CH(CH_3)_2$ | H | H | $SO_3M$ |
| 2,3- Substitution Product | H | $SO_3M$ | $SO_3M$ | H | H | H | H | H |
| | H | $SO_3M$ | $SO_3M$ | OH | H | H | H | H |
| | H | $SO_3M$ | $SO_3M$ | H | H | $NH_2$ | H | H |
| 2,6- Substitution Product | H | $SO_3M$ | H | H | H | $SO_3M$ | H | H |
| | OH | $SO_3M$ | H | H | H | $SO_3M$ | H | H |
| | H | $SO_3M$ | H | OH | H | $SO_3M$ | H | H |
| | $NH_2$ | $SO_3M$ | H | H | H | $SO_3M$ | H | H |
| 2,7- Substitution Product | H | $SO_3M$ | H | H | H | H | $SO_3M$ | H |
| | H | $SO_3M$ | H | $NHC=O(CH_3)$ | OH | H | $SO_3M$ | H |
| | H | $SO_3M$ | H | $NHC=OC_6H_5$ | OH | H | $SO_3M$ | H |
| | H | $SO_3M$ | H | OH | $NH_2$ | H | $SO_3M$ | H |
| | H | $SO_3M$ | H | OH | OH | H | $SO_3M$ | H |

TABLE 1-continued (VIII)

[Structure of naphthalene with R30-R37 substituents]

| Position of Sulfonic acid group | R30 | R31 | R32 | R33 | R34 | R35 | R36 | R37 |
|---|---|---|---|---|---|---|---|---|
| | H | $SO_3M$ | H | OH | $OC_2H_5$ | H | $SO_3M$ | H |
| | H | $SO_3M$ | H | $NHC{=}O(CH_3)$ | $OC{=}O(CH_3)$ | H | $SO_3M$ | H |
| | H | $SO_3M$ | H | I | H | H | $SO_3M$ | H |
| | H | $SO_3M$ | OH | H | H | OH | $SO_3M$ | H |
| | H | $SO_3M$ | H | OH | H | H | $SO_3M$ | H |
| | H | $SO_3M$ | OH | H | H | H | $SO_3M$ | H |
| | H | $SO_3M$ | H | $NH_2$ | H | H | $SO_3M$ | H |

Another concrete example of the organic acid is a benzene derivative represented by the following chemical formula (IX). $R^{38}$ to $R^{43}$ are groups shown in Table 2.

If J in the chemical formula (II) is a carbon atom, the silicon complex compound may be represented by the following chemical formula (XI).

TABLE 2

(IX)

[Structure of benzene with R38-R43 substituents]

| Position of Sulfonic acid group | R38 | R39 | R40 | R41 | R42 | R43 |
|---|---|---|---|---|---|---|
| 1,2-Substitution Product | $SO_3M$ | $SO_3M$ | H | H | H | H |
| | $SO_3M$ | $SO_3M$ | H | $NH_2$ | H | H |
| | $SO_3M$ | $SO_3M$ | H | $OC_6H_5$ | H | $C_{12}H_{25}$ |
| | $SO_3M$ | $SO_3M$ | H | $OC_6H_4(C_{12}H_{25})$ | H | H |
| 1,3-Substitution Product | $SO_3M$ | H | $SO_3M$ | H | H | H |
| | $SO_3M$ | H | $SO_3M$ | H | OH | OH |
| | $SO_3M$ | H | $SO_3M$ | H | $CH_3$ | H |
| | $SO_3M$ | H | $SO_3M$ | H | COOH | H |
| | $SO_3M$ | H | $SO_3M$ | H | H | $NH_2$ |
| 1,4-Substitution Product | $SO_3M$ | H | H | $SO_3M$ | H | H |
| | $SO_3M$ | $NH_2$ | H | $SO_3M$ | H | H |

If J in the chemical formula (I) is a carbon atom, the silicon complex compound may be represented by the following chemical formula (X).

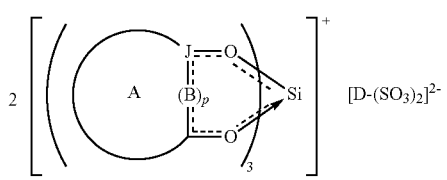

(X)

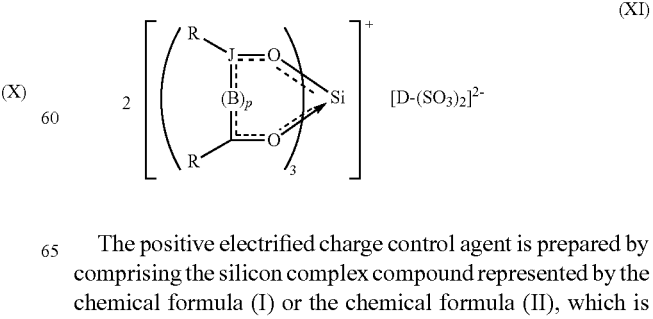

(XI)

The positive electrified charge control agent is prepared by comprising the silicon complex compound represented by the chemical formula (I) or the chemical formula (II), which is obtained by forming a salt between the silicon complex cation and the organic anion having at least two sulfonic acid groups, as an effective component.

The silicon complex compound is prepared by combining a well-known method.

For example, the silicon complex compound represented by the chemical formula (I) is prepared by the following method. As the first step, a silicification agent such as tetraethoxysilane or a silicon halide illustrated with silicon tetrachloride is allowed to be reacted with a compound having hydroxyl group and carbonyl group represented by the following chemical formula (XII).

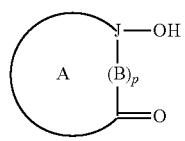
(XII)

In the chemical formula (XII), p, B, J and A are the same as the chemical formula (I). The oxygen derived from the hydroxyl group is combined with the central silicon atom derived from the silicification agent by the covalent bond, and the carbonyl group is combined with the central silicon atom by the coordination bond. Then, a silicon complex intermediate represented by the following chemical formula (XIII) is obtained.

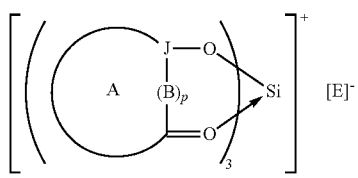
(XIII)

In the chemical formula (XIII), p, B, J and A are the same as the chemical formula (I), and $[E]^-$ is an anion. $[E]^-$ is an anion derived from the silicification agent generally.

It is preferable that the silicon halide such as a silicon tetrachloride is used as the silicification agent in order to obtain the silicon complex intermediate with high yield and high purity. For example, if the silicon tetrachloride is reacted with the compound represented by the chemical formula (XII), $[E]^-$ in the chemical formula (XIII) is a halogen anion $[X]^-$ such as chloride ion $Cl^-$, as shown in the chemical formula (V).

As the following second step, the silicon complex intermediate is reacted with $D-(SO_3M)_2$ of the organic acid having at least two sulfonic acid groups or of the salt thereof, and $[E]^-$ in the silicon complex intermediate represented by the chemical formula (XIII) such as $[X]^-$ is ion-changed into $[D-(SO_3)_2]^{2-}$ of the organic acid anion having at least two sulfonic acid groups, to obtain the silicon complex compound represented by the chemical formula (I).

The example of preparing the silicon complex compound represented by the chemical formula (I) is described, and the silicon complex compound represented by the chemical formula (II) is prepared similarly.

The important feature of the present invention is that a counter ion in the silicon complex compound is the organic acid having at least two sulfonic acid groups. The positive electrified charge control agent comprising the silicon complex compound of the present invention has a predominant effect of improving an electrification property, heat stability and environmental stability, as compared with a charge control agent whose counter ion is an anion other than the organic acid having at least two sulfonic acid groups, for example a chloride anion to which the present invention is not applied.

In addition, it is an important factor for improving the electrification property of the positive electrified charge control agent that a content of allowable residual halogen derived from the compound represented by the chemical formula (V) or the chemical formula (VI) is 0.2% or less, preferably 0.1% or less when the ion-changing reaction is performed. The electrification property, the preservation stability and the environmental resistance thereof improve more resulting from a preferable embodiment that there are few contents of allowable residual halogen.

As concrete examples of silicon complex compounds represented by the chemical formula (I) or the chemical formula (II) are shown below. However, the present invention is certainly not limited to these examples.

Compound Example 1

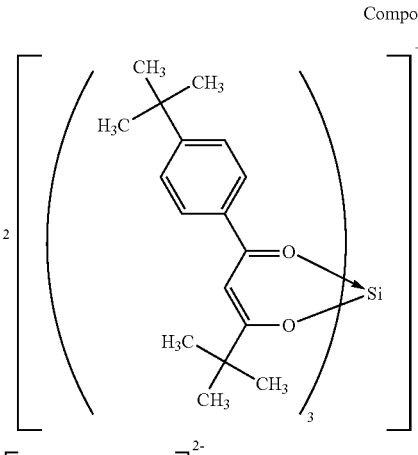

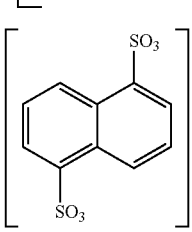

Compound Example 2

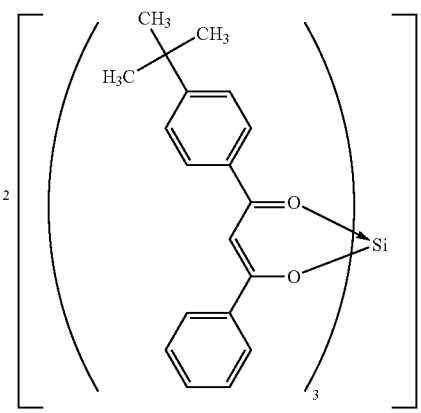

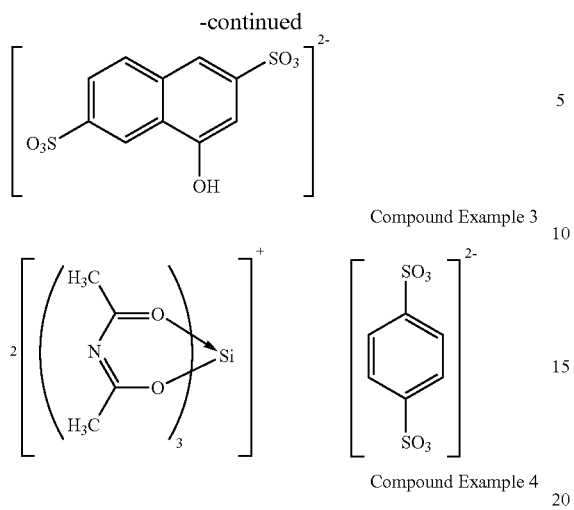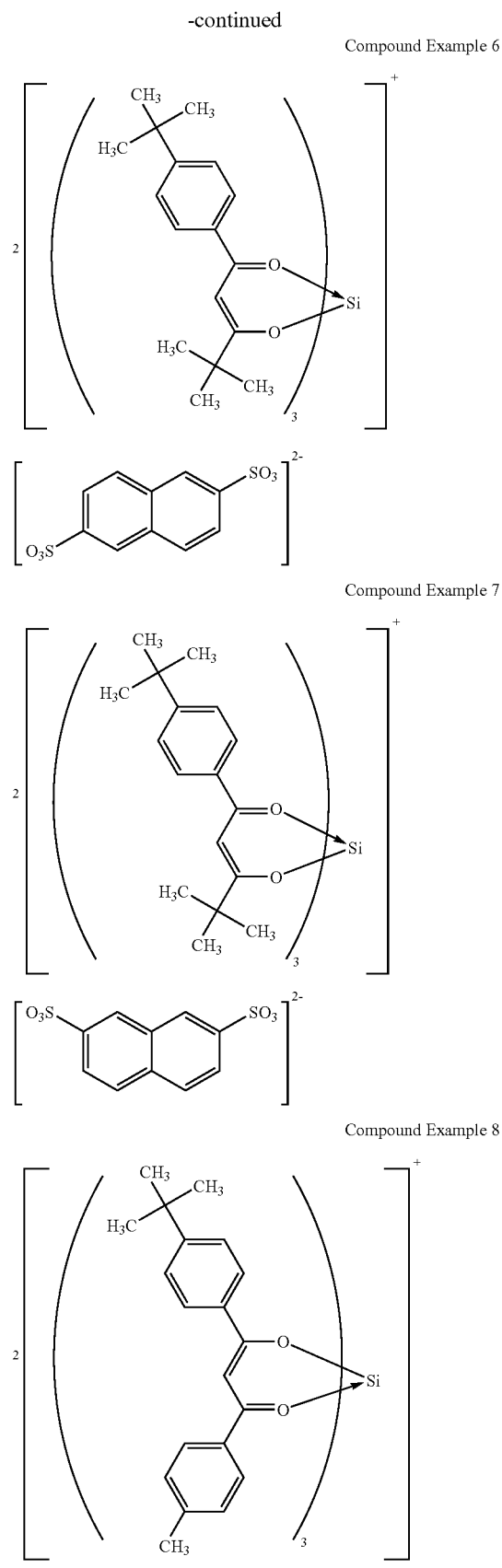

-continued
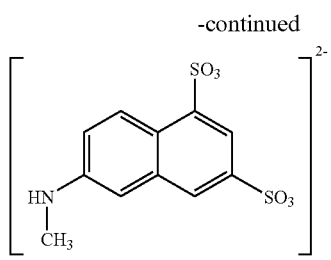
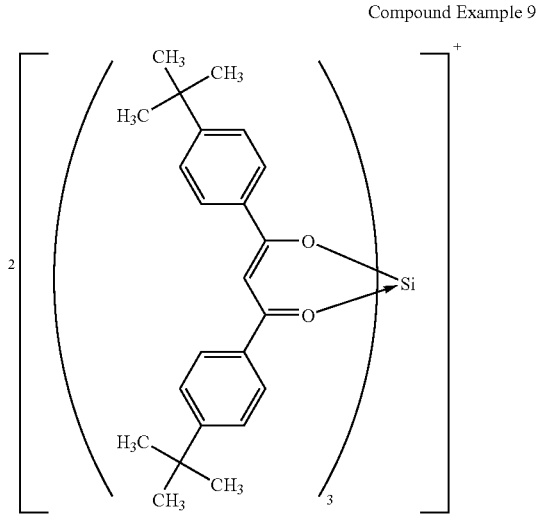
Compound Example 9
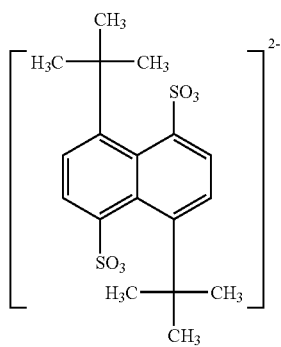
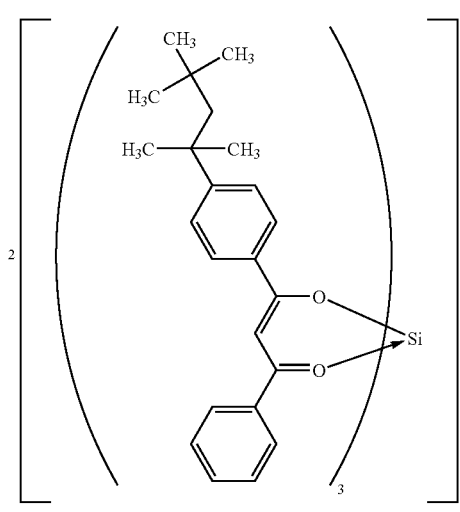
Compound Example 10
-continued
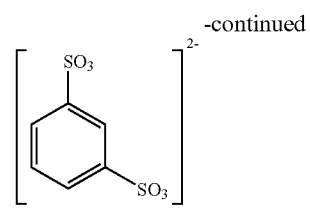
Compound Example 11
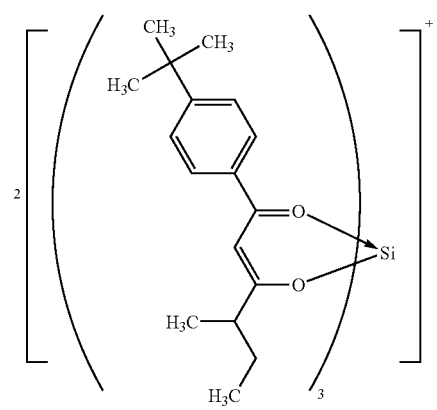
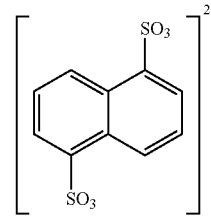
Compound Example 12
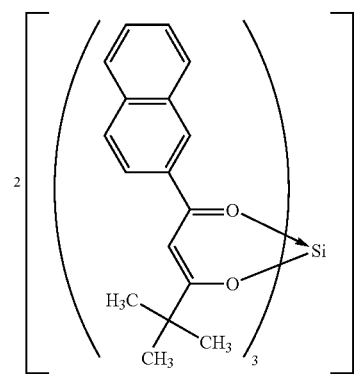
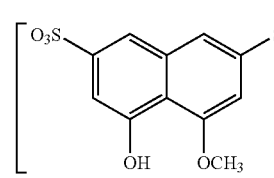
Compound Example 13
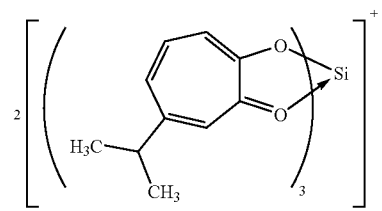

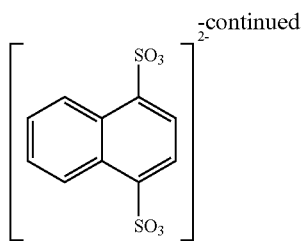
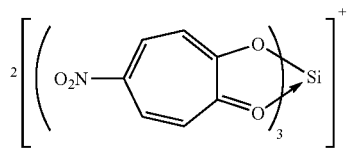
Compound Example 14
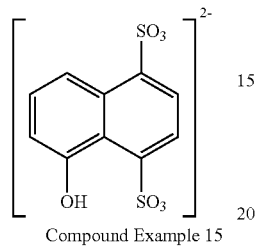
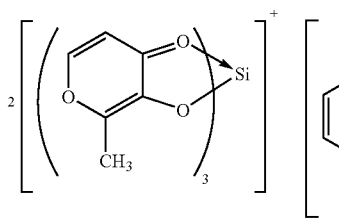
Compound Example 15
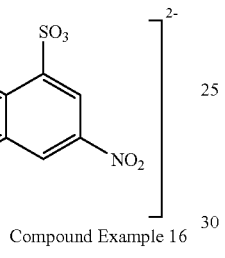
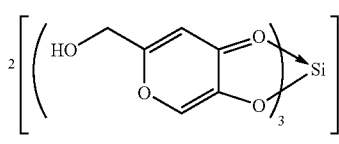
Compound Example 16
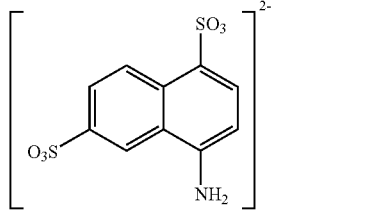
Compound Example 17
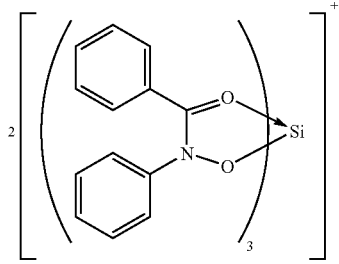
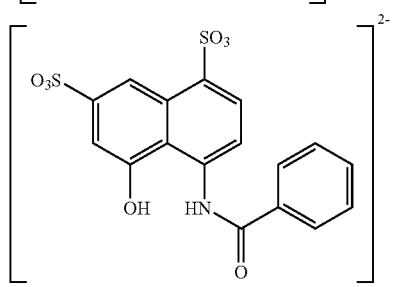
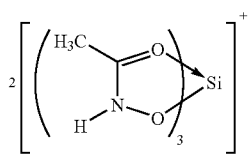
Compound Example 18
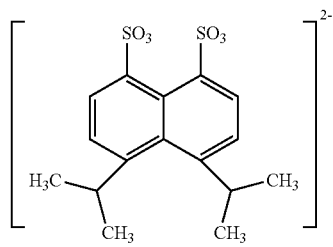
Compound Example 19
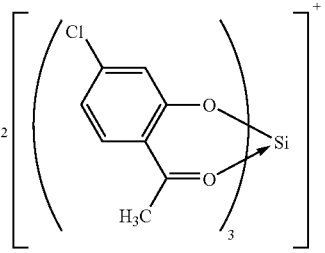
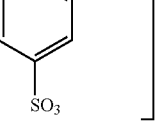
Compound Example 20
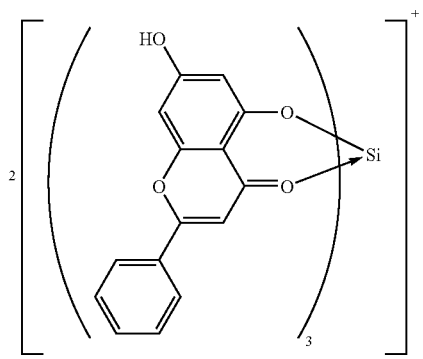
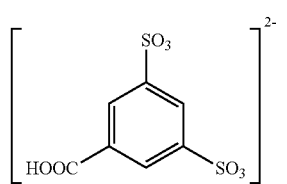

-continued
Compound Example 21
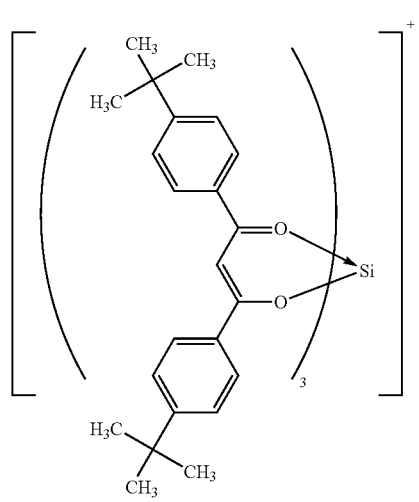
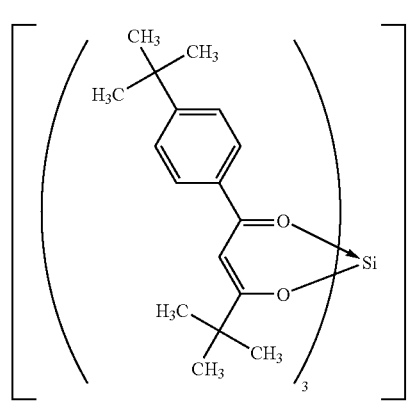
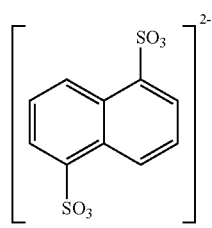
Compound Example 22
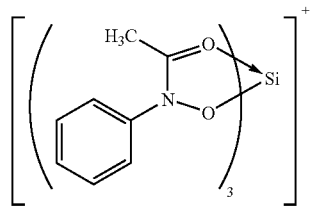
-continued
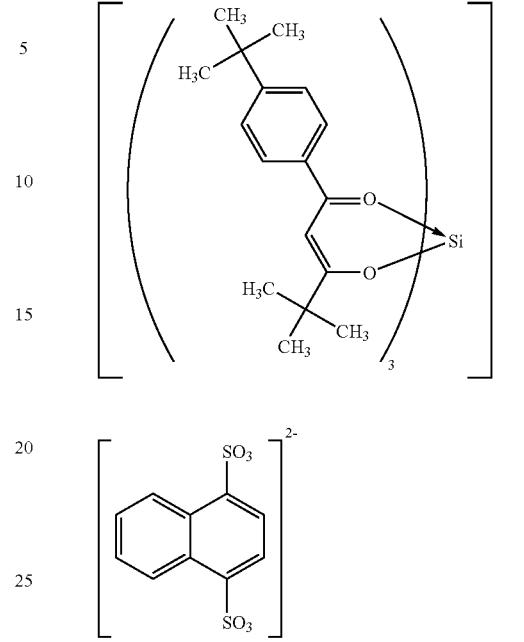
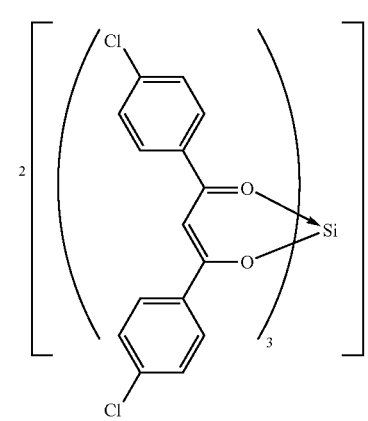
Compound Example 23
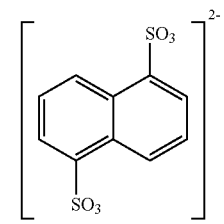
Compound Example 24
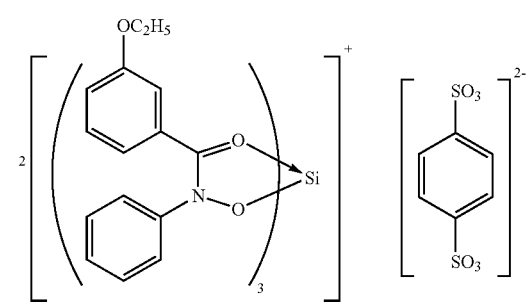

-continued
Compound Example 25
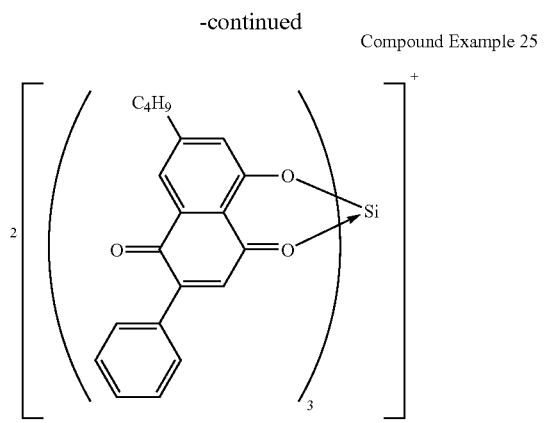
Compound Example 26
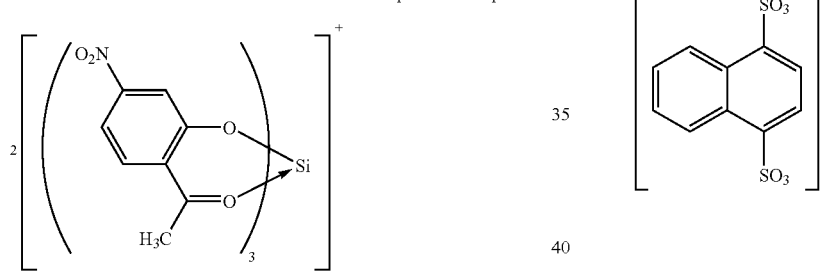
Compound Example 27
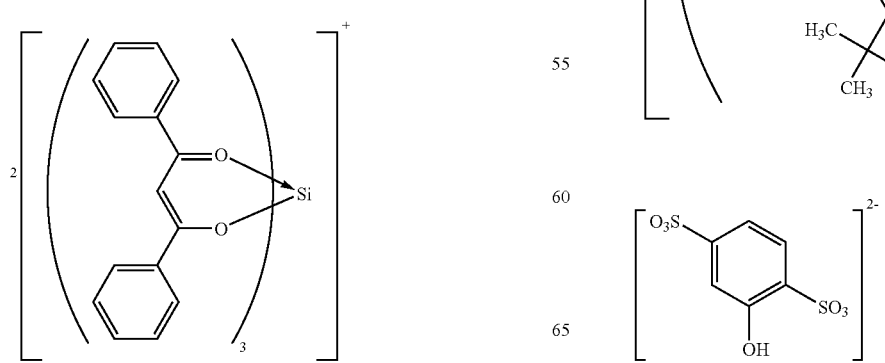
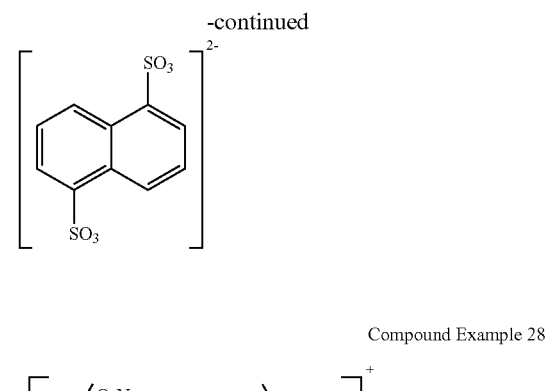
Compound Example 28
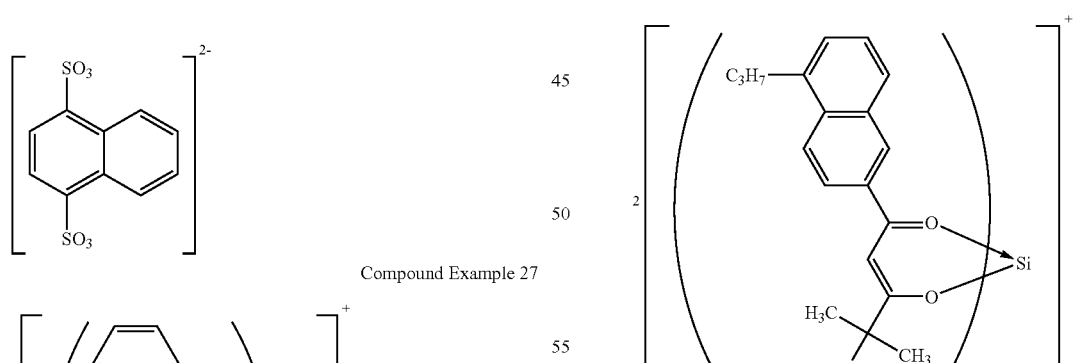
Compound Example 29
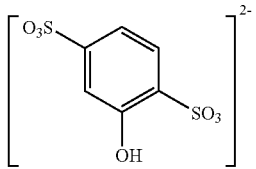

-continued

Compound Example 30

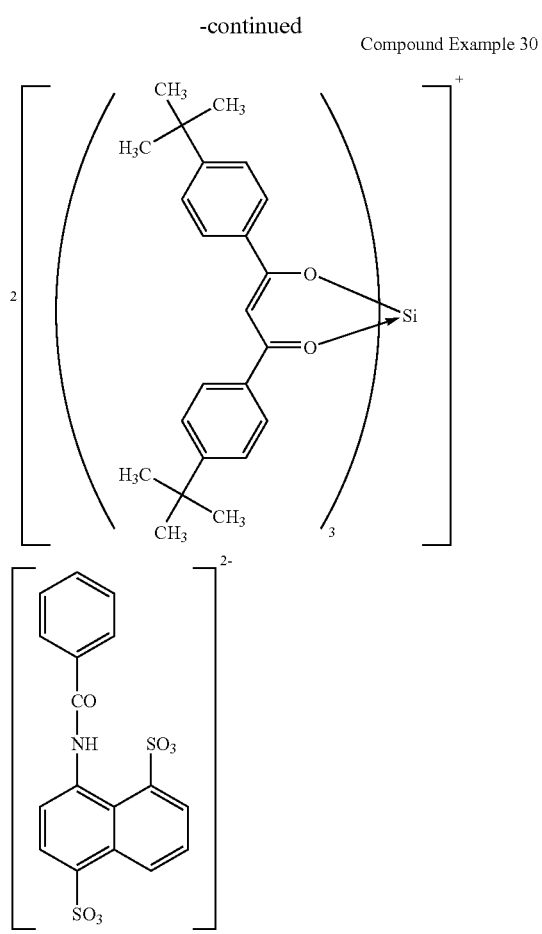

The positive electrified charge control agent may comprise the sole compound or may comprise the plural compounds having different structure to each other. The positive electrified charge control agent may comprise silicon complex compounds comprising plural different silicon complexes or a silicon complex as a compound of higher order having plural different bivalent anion of organic acids. Furthermore, the positive electrified charge control agent may comprise conventional charge control agents together.

The positive electrified toner for developing an electrostatic image of the present invention comprises the above-mentioned positive electrified charge control agent.

It is preferable that the positive electrified toner for developing an electrostatic image comprises 0.1 to 10 parts by weight of the positive electrified charge control agent and 100 parts by weight of the resin for the toner. It is much preferable that 0.5 to 5 parts by weight of the charge control agent is comprised in the toner. The toner may further comprise the colorant.

The positive electrified toner for developing the electrostatic image is preferably the toner that the charge control agent and the colorant are added internally and kneaded to the resin for the toner. Guest particles including the charge control agent may adhere to the surface of host particles including the resin for the toner and the colorant. The host particles may include the charge control agent, and the guest particles may include the resin for the toner.

The charge control method of the positive electrified toner for developing the electrostatic image of the present invention comprises a step for making the above-mentioned toner positively electrified by friction.

The silicon complex compound represented by the chemical formula (I) or the chemical formula (II) in the positive electrified charge control agent has the structure of that two ions comprising univalent silicon complex cation are combined with one ion comprising bivalent organic acid anion. Depending on the kind of the anion as the counter ion, the silicon complex compound achieves heat stability and environmental stability of the toner sufficiently when it is comprised in the toner. The property such as the heat stability and the environmental stability, which is indispensable for the charge control agent, improve much when the silicon complex compound has the above-mentioned structure, as compared with the case if the silicon complex compound comprises an anion component other than the sulfonic acid group.

Furthermore, resulting from the above-mentioned structure, the silicon complex compound represented by the chemical formula (I) or the chemical formula (II) has a feature of that the silicon complex compound hardly decomposes and the weight thereof hardly decreases even if the silicon complex compound is exposed under high temperature for a long time. Therefore, the positive electrified toner for developing the electrostatic image comprising the charge control agent of the present invention has very low possibility of generating a chemical substance derived from the charge control agent, which is harmful to a human body, into the exhaust gas at the time of printing, so a load and safety to the environment of the toner are excellent.

A volume resistivity of the silicon complex compound represented by the chemical formula (I) or the chemical formula (II) is preferably $1.0 \times 10^{13}$ to $5.0 \times 10^{15} \Omega \cdot cm$, much preferably $1.0 \times 10^{14}$ to $5.0 \times 10^{15}$ $\Omega \cdot cm$. The positive electrified toner for developing the electrostatic image comprising the charge control agent has stable electrification property and can adjust an amount of electrification or an electrification speed of the toner to a necessary suitable level.

The positive electrified toner for developing an electrostatic image comprising the charge control agent has an excellent electrification stability, an excellent preservation stability and an excellent environmental resistance. The image developed using the electrified toner has an excellent quality. Furthermore, the toner has little change of the amount of electrification of the toner under environmental change or hard environment of from high temperature and high humidity to low temperature and low humidity because of comprising the positive electrified charge control agent. Therefore, the toner has an excellent environmental stability.

The positive electrified toner for developing the electrostatic image of the present invention comprises the charge control agent, the resin for the toner and the colorant. If necessary to improve quality of the toner, the toner appropriately comprises a magnetic material, a fluid improvement agent or an offset prevention agent.

Examples of the resin for the toner are a commercial binding resin such as a thermoplastic resin illustrated with a styrene resin, a styrene-acrylate resin, a styrene-butadiene resin, a styrene-maleic acid resin, a styrene-vinylmethylether resin, a styrene-methacrylate copolymer, a polyester resin, a polypropylene resin; a thermosetting resin illustrated with a phenol resin, an epoxy resin. The exemplified resin may be used solely or plurally with blending.

The resin for the toner may be used to mix for the toner for full color by subtractive mixture of color stimuli, or the toner for an overhead projector (OHP). For the sake of that, it is required that the resin for the toner has transparency, is nearly colorless to a point in which color tone obstruction of toner images is not generated, has excellent compatibility with the charge control agent, fluidity under proper heat or pressure and possibility of fining. It is preferable that the resin for the toner is a styrene resin, an acrylate resin, a styrene-acrylate resin, a styrene-(meth)acrylate copolymer, or a polyester resin.

An electric charge of resin powder paint for electrostatic paint can be controlled or reinforced by adding the charge control agent of the present invention to the resin powder paint for electrostatic paint. The resin powder paint for electrostatic paint comprising the charge control agent of the present invention has an excellent heat resistance and an excellent reinforcement property, so it indicates high transfer efficiency even if the resin powder paint does not be recovered or does not be reused. Moreover, painting using the resin powder paint is performed by the general electrostatic powder painting methods such as a corona discharge system, a frictional electrification system, or a hybrid system.

Examples of the resin in the paint are a thermoplastic resin illustrated with an acrylate resin, a polyolefin resin, a polyester resin, a polyamide resin; a thermosetting resin illustrated with a phenol resin, an epoxy resin. The exemplified resin may be used solely or plurally with blending.

A dye and/or a pigment may be used solely or plurally with blending, as the colorant for the toner for color or for the electrostatic powder paint.

Examples of the colorant for the toner for color are organic pigment such as quinophtharone yellow, hansa yellow, isoindolinone yellow, benzidine yellow, perinone orange, perinone red, perylene maroon, rhodamine 6G lake, quinacridone red, rose bengale, copper phthalocyanine blue, copper phthalocyanine green, diketopyrrolopyrrole; inorganic pigment and metallic powder such as carbon black, titanium white, titanium yellow, ultramarine, cobalt blue, red iron oxide, aluminum powder, bronze; oil soluble dye and disperse dye such as an azo dye, a quinophthalone dye, an anthraquinone dye, a xanthene dye, a triphenylmethane dye, phthalocyanine dye, indophenol dye, indoaniline dye; triarylmethane dye modified with a resin illustrated as rosin, phenol that modified by rosin, maleic acid that modified by rosin; a dye and a pigment processed with higher fatty acid or resin and so on. The colorant may be used for the toner for color solely or plurally with blending. The dye and pigment having excellent spectral characteristics are used for regulation of the primary colors toner for full color suitably.

Moreover, examples of the colorant for the toner for chromatic mono-color are combinations of pigment and dye of similar colors such as suitable combination of rhodamine pigment and dye, quinophthalone pigment and dye, phthalocyanine pigment and dye.

Examples of the magnetic material are ferromagnetic particulates such as iron, cobalt, and ferrite. Examples of the fluid improvement agent are silica, aluminum oxide, and titanium oxide. Examples of the offset prevention agent are wax and olefin wax having low molecular weight.

The positive electrified toner for developing the electrostatic image is manufactured as follows. The charge control agent, the resin for the toner, the colorant, if necessary the magnetic material, the fluid improvement agent, or the offset prevention agent, are sufficiently mixed by a blender such as a ball mill. It is kneaded with melting by a heat-kneading machine such as a heating roll, a kneader or an extruder. After carrying out the cooling solidification thereof, it is granulated and classified to obtain the unary toner which is the toner particles by the granulation method, having the average particle size ranging from 5 to 20 microns.

The toner particles can be manufactured by a preparing method under spraying and drying of a solution of each component, a suspension polymerization method, or an emulsion polymerization method. The suspension polymerization method is as follows. A monomer of the resin for the toner, the charge control agent, the colorant, and if necessary the magnetic material, the fluid improvement agent, the offset prevention agent, and an additive agent such as a polymerization initiator, a cross linking agent and a mold release agent are solved or dispersed homogeneously, to obtain a monomer composition. The composition is carried out polymerization reaction in continuous phase including a dispersion stabilizer such as aqueous phase with dispersing by a dispersion apparatus, to obtain the toner particles having desired particle size.

Examples of the monomer are styrene derivative such as styrene, methylstyrene; (meth)acrylate such as methyl acrylate, ethyl acrylate, ethyl methacrylate, n-butyl methacrylate; vinyl monomer such as acrylonitrile, methacrylonitrile, acrylamide.

Examples of dispersion stabilizer are a surface active agent such as sodium dodecylbenzenesulfonate; an organic dispersion agent such as polyvinyl alcohol, methyl cellulose, methylhydroxypropyl cellulose; an inorganic dispersion agent such as fine powder of polyvalent metal phosphate illustrated by calcium phosphate, magnesium phosphate and aluminum phosphate, fine powder of carbonate illustrated by calcium carbonate and magnesium carbonate; calcium metasilicate, calcium sulfate, barium sulfate, calcium hydroxide, aluminum hydroxide.

Examples of the polymerization initiator are azo or diazo initiators such as 2,2'-azoisobutyronitrile, azobisbutyronitrile; peroxide initiator such as benzoyl peroxide.

Moreover, the positive electrified toner for developing the electrostatic image is also manufactured as follows. The host particles are the toner particles including the charge control agent by the above-mentioned granulation or polymerization method. The guest particles consisting of the particles of the charge control agent, or the guest particles including the particles which the charge control agent of 10 to 90 percent by weight is dispersed into the resin having dispersibility of the charge control agent, make adhesion to the surfaces of the host particles to obtain the toner.

Examples of the method that the guest particles make adhesion to the surfaces of the host particles are an external addition method, and a method that the guest particles are stuck to the host particles by a hybridization system. Examples of the resin having dispersibility of the charge control agent are a styrene resin, a styrene-acrylate resin, a styrene-butadiene resin, a styrene-maleic resin, a styrene-methylvinylether resin, a styrene-methacrylate copolymer, a phenol resin, an epoxy resin, a paraffin wax, an acrylate resin and a polyester resin. The exemplified resin may be used solely or plurally with blending.

Although the examples that the host particles are the toner particles including the charge control agent by the granulation method or the polymerization method are described, the host particles may be the toner including no charge control agent by the granulation method or the polymerization method.

A binary component developer using the positive electrified toner for the electrostatic image development is prepared with mixing the toner and a carrier. This developer is used for developing by a binary component magnetic brush development method and so on. Examples of the carrier are powder of iron or nickel or magnetite or ferrite and glass beads whose particle size is ranging from 50 to 200 microns, the modified powder thereof or the modified beads thereof whose surfaces are coated with an acrylate copolymer, a styrene-acrylate copolymer, a styrene-methacrylate copolymer, a silicone resin, a polyamide resin or a fluoroethylene resin.

A unary component developer using the positive electrified toner for the electrostatic image development is prepared with adding and dispersing appropriate ferromagnetic particulates such as powder of iron or nickel or ferrite on the occasion of preparing the toner. This developer is used for developing by a contact development method or a jumping development method.

Hereunder, embodiments of the present invention are explained in detail. The invention is not limited to these embodiments.

The following synthetic examples 1 to 6 indicate embodiments of the synthesis of the silicon complex compound used for the charge control agent to which this invention is applied.

SYNTHETIC EXAMPLE 1

(1-1) Synthesis of a Silicon Complex Intermediate 160.0 g (0.614 mol) of 1-(4'-tert-butylphenyl)-4,4-dimethylpentane-1,3-dion was dissolved in 800 ml of ethyl acetate. 34.8 g (0.204 mol) of silicon tetrachloride was added dropwise thereto at the room temperature. It was refluxed for 2 hours and cooled, and then precipitated white crystals were filtrated. The crystals were washed with 600 ml of ethyl acetate and then washed with 2000 ml of water. The crystals were dried at 80° C. for 24 hours to obtain 107.4 g (0.128 mol) of the silicon complex intermediate of Compound Example a represented by the following chemical formula.

Compound Example a

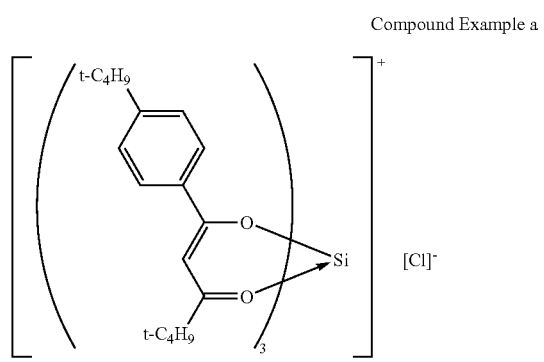

The data of measurement result of the obtained silicon complex intermediate of the Compound Example a by the liquid chromatography mass spectrometric analysis (LC/MS) using M-8000 TYPE LC/3DQMS that is available from Hitachi, Ltd. is shown in FIG. 1. An actual value m/z is 806.13 of the obtained intermediate as FIG. 1 and mostly identical with 806.2 of the theoretical value which the chloride ion is eliminated from the desired Compound Example a having 841.6 of the theoretical value. Therefore, the intermediate is identified as the desired Compound Example a.

(1-2) Anion Exchange 28 g (33.7 mmol) of the silicon complex intermediate of Compound Example a was dispersed into mixed solvent of water and methanol. 5.72 g (17.2 mmol) of 1,5-naphthalene-disulfate disodium salt was added thereto and dispersed for 24 hours at the room temperature. Obtained reactant was filtrated and washed with water until the electric conductivity of the filtrate lowered. It was dried at 80° C. to obtain 30.9 g (16.3 mmol) of the silicon complex compound represented by the Compound Example 1.

(1-3) Identification

Figure 2:
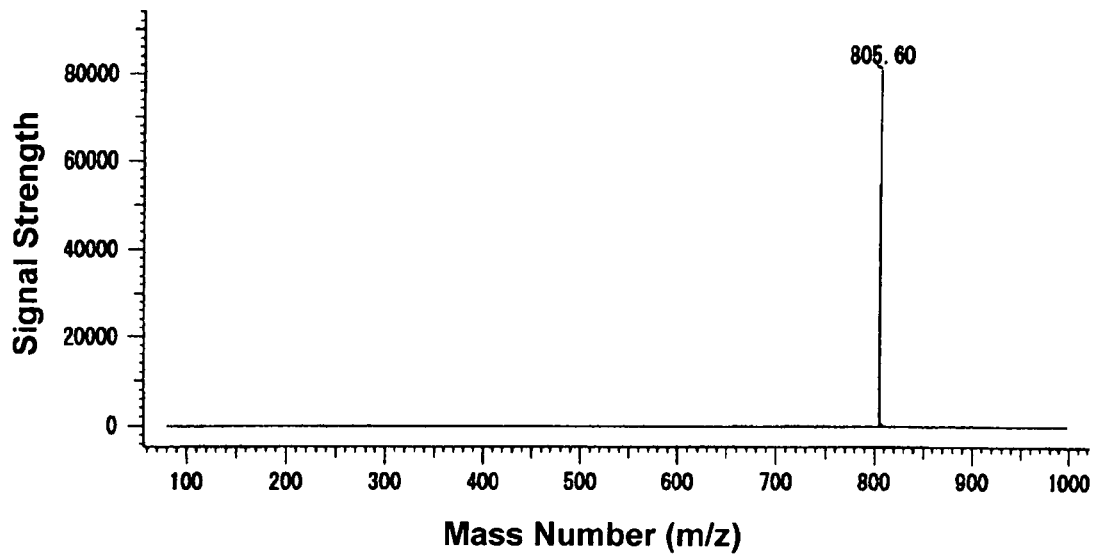
FIG. 2 is a figure showing a measurement result of one of peak by a liquid chromatography mass spectrometric analysis of a silicon complex compound of Compound Example 1 comprised in a positive electrified charge control agent to which the present invention is applied.
Figure 3:
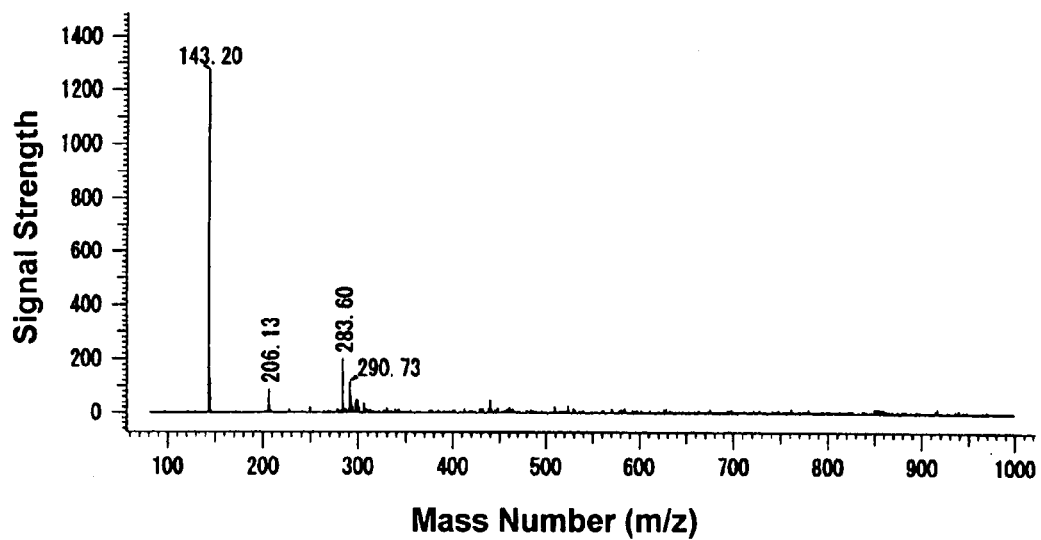
FIG. 3 is a figure showing a measurement result of another peak by a liquid chromatography mass spectrometric analysis of a silicon complex compound of Compound Example 1 comprised in a positive electrified charge control agent to which the present invention is applied.

The data of measurement result of the obtained silicon complex compound of the Compound Example 1 by the liquid chromatography mass spectrometric analysis (LC/MS) using M-8000 TYPE LC/3DQMS System that is available from Hitachi, Ltd. is shown in FIG. 2. An actual value m/z of one of peaks of the liquid chromatography is 805.60 as FIG. 2 and mostly identical with 806.15 as half of 1612.3 of the theoretical value that the 1,5-naphthalenedisulfonic acid is eliminated from the desired Compound Example 1 having 1898.6 of the theoretical value. An actual value m/z of another peak is 143.20 as FIG. 3 and mostly identical with 143.15 as half of 286.3 of the theoretical value of the 1,5-naphthalenedisulfonic acid anion of the bivalent anion. Furthermore, according to CHS elemental analysis of the silicon complex compound of the Compound Example 1, the content of C in the compound was 70.54% (theoretical value: 70.85%), the content of H in the compound was 7.91% (theoretical value: 7.64%), and the content of S in the compound was 3.40% (theoretical value: 3.38%), and they were mostly identical with the theoretical values. Therefore, the obtained silicon complex compound is identified as the desired Compound Example 1.

(1-4) Analysis of Chlorine

A content of allowable residual chlorine in the obtained silicon complex compound was measured by coulometry system using chlorine-sulfur measurement apparatus of TOX-10 sigma that is available from Mitsubishi Kasei Corporation. The content of allowable residual chlorine in the silicon complex compound was 770 ppm.

(1-5) Thermal Analysis

A rate of weight-decrease of the obtained silicon complex compound after heating for 2 hours under 180° C. was measured by a thermal analysis of isothermal mass-change method using a differential thermal-thermogravimetric simultaneous measurement apparatus of TG/DTA6200 that is available from SII NanoTechnology Inc. The rate of weight-decrease of the silicon complex compound was 4.9%.

(1-6) Measurement of Volume Resistivity

A volume resistivity of the obtained silicon complex compound was measured under the following condition.

Test condition: 23±2° C., 50±5% RH
Testing machine: Digital ultra-high resistance/Microammeter R8340A type that is available from Advantest Corporation.
Applied voltage and Time: 500V (DC), 1 minute
Electrode: Main electrode having 38 mm of the diameter
Number of test: n=1
Load: the sample was compressed to 2000 kg The proper volume resistivity of the silicon complex compound was $4.37 \times 10^{14}$ Ω·cm.

SYNTHETIC EXAMPLE 2

(2-1) Synthesis of a Silicon Complex Intermediate 50.0 g (0.223 mol) of dibenzoylmethane was dissolved in 250 ml of toluene. 12.6 g (0.074 mol) of silicon tetrachloride was added dropwise thereto at the room temperature. It was reacted at 50° C. for 5 hours and cooled, and then precipitated pastel yellow crystals were filtrated. The crystals were washed with 500 ml of toluene and then washed with 500 ml of water. The crystals were dried at 80° C. for 24 hours to obtain 44.8 g (0.061 mol) of the silicon complex intermediate of Compound Example b represented by the following chemical formula.

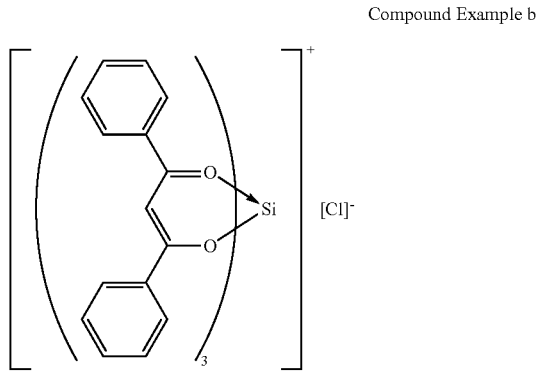

Compound Example b

Figure 4:
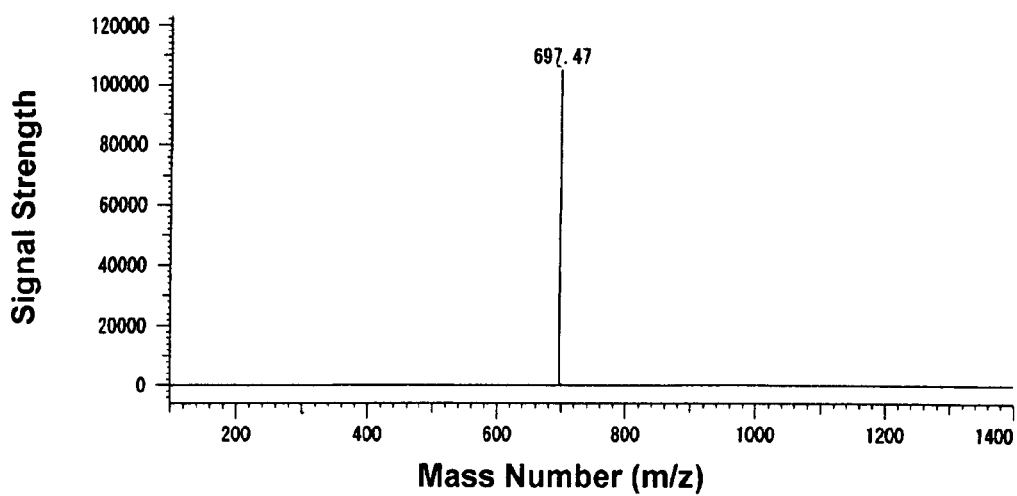
FIG. 4 is a figure showing a measurement result by a liquid chromatography mass spectrometric analysis of an intermediate of a silicon complex compound of Compound Example 27 comprised in a positive electrified charge control agent to which the present invention is applied.

The data of measurement result of the silicon complex intermediate of the Compound Example b by the liquid chromatography mass spectrometric analysis (LC/MS) using M-8000 TYPE LC/3DQMS that is available from Hitachi, Ltd. is shown in FIG. 4. An actual value m/z of the obtained intermediate is 697.47 as FIG. 4 and mostly identical with 697.78 of the theoretical value which the chloride ion is eliminated from the desired Compound Example b having 733.28 of the theoretical value. Therefore, the obtained intermediate is identified as the desired Compound Example b.

(2-2) Anion Exchange 20 g (27.3 mmol) of the silicon complex intermediate of Compound Example b was dispersed into mixed solvent of water and methanol. 4.62 g (13.9 mmol) of 1,5-naphthalenedisulfate disodium salt was added thereto and dispersed for 24 hours at the room temperature. Obtained reactant was filtrated and washed with water until the electric conductivity of the filtrate lowered. It was dried at 80° C., to obtain 21.5 g (12.8 mmol) of the silicon complex compound represented by the Compound Example 27.

(2-3) Identification

Figure 5:
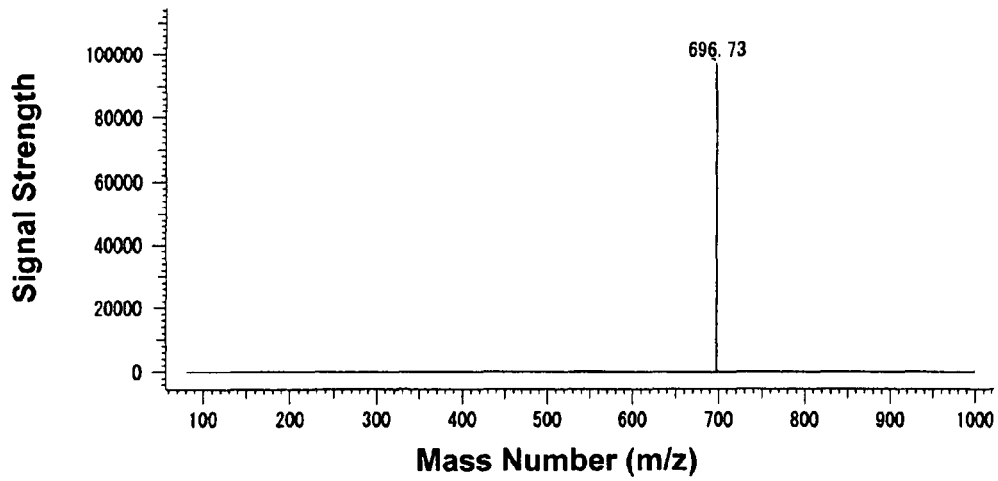
FIG. 5 is a figure showing a measurement result of one of peak by a liquid chromatography mass spectrometric analysis of a silicon complex compound of Compound Example 27 comprised in a positive electrified charge control agent to which the present invention is applied.
Figure 6:
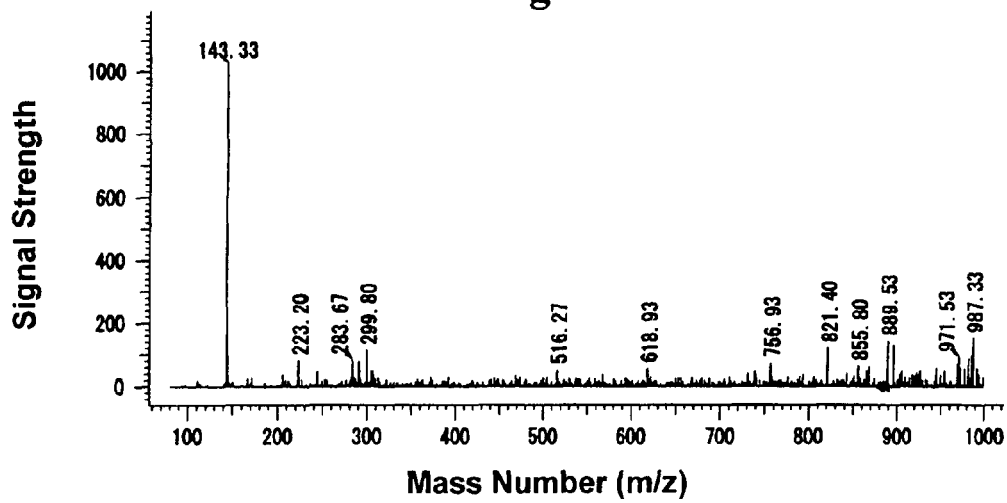
FIG. 6 is a figure showing a measurement result of another peak by a liquid chromatography mass spectrometric analysis of a silicon complex compound of Compound Example 27 comprised in a positive electrified charge control agent to which the present invention is applied.

The data of measurement result of the obtained silicon complex compound of the Compound Example 27 by the liquid chromatography mass spectrometric analysis (LC/MS) using M-8000 TYPE LC/3DQMS that is available from Hitachi, Ltd. is shown in FIG. 5. An actual value m/z of the silicon complex compound is 696.73 as FIG. 5 and mostly identical with 697.8 as half of 1395.6 of the theoretical value which the 1,5-naphthalenedisulfonic acid is eliminated from the desired Compound Example 27 having 1681.9 of the theoretical value. An actual value m/z of another peak is 143.33 as FIG. 6 and mostly identical with 143.15 as half of 286.3 of the theoretical value of the 1,5-naphthalenedisulfonic acid anion of the bivalent anion. Furthermore, according to CHS elemental analysis of the silicon complex compound of the Compound Example 27, the content of C in the compound was 71.15% (theoretical value: 71.41%), the content of H in the compound was 4.35% (theoretical value: 4.31%), and the content of S in the compound was 3.85% (theoretical value: 3.81%), and they were mostly identical with the theoretical values. Therefore, the obtained silicon complex compound is identified as the desired Compound Example 27.

(2-4) Analysis of Chlorine, (2-5) Thermal Analysis and (2-6) Measurement of Volume Resistivity A content of allowable residual chlorine, a rate of weight-decrease and a volume resistivity of the obtained silicon complex compound were measured in the same procedure as the above-mentioned procedure. The content of allowable residual chlorine in the silicon complex compound was 336 ppm. The rate of weight-decrease of the silicon complex compound after heating for 2 hours under 180° C. was 4.4%. The proper volume resistivity of the silicon complex compound was $2.8 \times 10^{15}$ Ω·cm.

SYNTHETIC EXAMPLE 3

Synthesis of Compound Example 4

25 g (80.5 mmol) of 4-t-butyl-4'-methoxydibenzoyl-methane was dissolved in 250 ml of toluene. 4.56 g (26.8 mmol) of silicon tetrachloride was added thereto. It was reacted at 50° C. for 4 hours and cooled, and then precipitated yellow crystals were filtrated. The crystals were washed with 200 ml of toluene and then washed with 400 ml of water. The crystals were dried at 80° C. for 24 hours to obtain the silicon complex intermediate. 10 g (10.1 mmol) of the obtained silicon complex intermediate was dispersed into mixed solvent of water and methanol. 1.76 g (5.07 mmol) of 4-amino-2,7-naphthalenedisulfate disodium salt was added thereto and dispersed for 24 hours at the room temperature to obtain 11.0 g (4.97 mmol) of the silicon complex compound represented by the Compound Example 4.

SYNTHETIC EXAMPLE 4

Synthesis of Compound Example 5

20 g (89.2 mmol) of dibenzoylmethane was dissolved in 80 ml of toluene. 20 ml of toluene solution in which 5.05 g (29.7 mmol) of silicon tetrachloride was dissolved, was added dropwise thereto. It was reacted at 50° C. for 4 hours and cooled, and then precipitated pastel yellow crystals were filtrated. The crystals were washed with 200 ml of toluene and then washed with 100 ml of tetrahydrofuran, and then further washed with 100 ml of water. It was dried at 80° C. for 24 hours to obtain the silicon complex intermediate. 10 g (13.6 mmol) of the obtained silicon complex intermediate was dispersed into mixed solvent of water and methanol. 2.48 g (6.8 mmol) of 4,5-dihydroxy-2,7-naphthalenedisulfate disodium salt was added thereto and dispersed for 24 hours at the room temperature to obtain 10.3 g (6.01 mmol) of the silicon complex compound represented by the Compound Example 5.

SYNTHETIC EXAMPLE 5

Synthesis of Compound Example 13

5.00 g (30.5 mmol) of hinokitiol was dissolved in 300 ml of hexane. 50 ml of hexane solution in which 1.72 g (10.2 mmol) of silicon tetrachloride was dissolved, was added dropwise thereto. It was refluxed for 1 hour and cooled, and then precipitated white crystals were filtrated. The crystals were washed with 300 ml of hexane and then dried under reduced pressure at 70° C. for 24 hours to obtain the silicon complex intermediate. 5.00 g (9.04 mmol) of the obtained silicon complex intermediate was dispersed into mixed solvent of water and methanol. 1.50 g (4.52 mmol) of 1,4-naphthalenedisulfate disodium salt was added thereto and dispersed for 24 hours at the room temperature, to obtain 5.10 g (3.86 mmol) of the silicon complex compound represented by the Compound Example 13.

SYNTHETIC EXAMPLE 6

Synthesis of Compound Example 17

4.00 g (18.8 mmol) of N-benzoyl-N-phenylhydroxyamine was dissolved in 20 ml of toluene. 20 ml of toluene solution in which 1.06 g (6.25 mmol) of silicon tetrachloride was dissolved, was added dropwise thereto. It was refluxed for 2 hours and cooled, and then precipitated white crystals were filtrated. The crystals were washed with 300 ml of toluene and then dried under reduced pressure at 70° C. for 24 hours to obtain the silicon complex intermediate. 3.87 g (5.53 mmol) of the obtained silicon complex intermediate was dispersed into mixed solvent of water and methanol. 1.29 g (2.77 mmol) of 4-(benzoylamino)-5-hydroxy-1,7-naphthalenedisulfate disodium salt was added thereto and dispersed for 24 hours at the room temperature to obtain 4.05 g (2.31 mmol) of the silicon complex compound represented by the Compound Example 17.

The various silicon complex compounds used for the positive electrified charge control agent to which this invention is applied were obtained by the same procedure as the above-mentioned procedure.

Examples 1 to 13 show the preparation of the positive electrified toner for developing the electrostatic image including the silicon complex compound of the charge control agent, and the formation of the image onto the paper using the toner.

EXAMPLE 1

100 parts by weight of styrene-acrylate copolymer resin: CPR-600B which is available from Mitsui Chemicals, Inc., 3 parts by weight of low grade polypropylene: VISCOL 550-P which is available from Sanyo Chemical Industries, Ltd., 5 parts by weight of color dye of magenta: C.I. Pigment Red 57:1, and 1 part by weight of the charge control agent comprising Compound Example 1, were pre-mixed homogeneously using a high speed mixer. The mixture was kneaded with melting by an extruder. It was cooled and granulated roughly by a vibration mill. The prepared rough granules were finely granulated using an air jet mill equipping with a classifier to obtain the magenta toner having 10 microns of the particle size thereof.

5 parts by weight of the obtained toner and 95 parts by weight of the carrier of ferrite powder: F-150 which is available from Powder Tech Corporation were mixed to prepare the developer.

After the developer was weighed in a plastic bottle, it was agitated at 100 rpm of rotating speed by a boll mill to be electrified. The quantity of the initial electrification (a value after three minutes) was measured under the condition of the atmosphere. And the electrification stability was evaluated by measuring the quantity of the frictional electrification at every agitation time (minute). The electrification stability was evaluated with two ranks. In case of excellent electrification stability, it was indicated as "O", and if in the other case, it was indicated as "X". The environmental stability of the electrification was evaluated by measuring the quantity of the electrification (a value after ten minutes) of the following developers in the same way: the developer humidified under the standard condition of 50% relative humidity at 25° C. for 24 hours or more, and the developers humidified under the low temperature and humidity condition of 30% relative humidity at 5° C. for 24 hours or more, and under the high temperature and humidity condition of 90% relative humidity at 35° C. for 24 hours or more. The environmental stability of the electrification was evaluated with three ranks. The value satisfying the following numerical equations was calculated.

{[(Quantity of Electrification under Standard Condition)−(Quantity of Electrification under Low Temperature and Humidity)]/(Quantity of Electrification under Standard Condition)}×100, or {[(Quantity of Electrification under Standard Condition)−(Quantity of Electrification under High Temperature and Humidity)]/(Quantity of Electrification under Standard Condition)}×100

And then in case an absolute value of a changing rate of the calculated value was 0.0 to 5.0, it was indicated as "O", in case the absolute value was 5.0 to 10.0, it was indicated as "Δ", in case the absolute value was 10.0 or more, it was indicated as "X".

The quantity of the electrification was measured using a measuring instrument TB-200 of a blow-off quantity of the electrification, which is available from Toshiba Chemical Corporation.

The images of the toner were formed using the developer by a commercial copying machine. Fogginess, reproducibility of fine lines, electrification stability and durability, and phenomenon of offset were visually observed as regards the formed images of the toner.

The images of the toner were evaluated with two ranks. In case of no fogginess, it was indicated as "O", and if in the other case, it was indicated as "X". In case of excellent reproducibility of fine lines, it was indicated as "O", and if in the other case, it was indicated as "X". In case of excellent electrification stability and durability, it was indicated as "O", and if in the other case, it was indicated as "X". In case of observation of no phenomenon of offset, it was indicated as "O", and if in the other case, it was indicated as "X".

The evaluation results are shown in Table 4.

EXAMPLES 2 TO 7

The positive electrified toners for developing the electrostatic image were prepared as same as Example 1 except for using Compound Example 2, Compound Example 6, Compound Example 7, Compound Example 8, Compound Example 13 or Compound Example 17 in Examples 2 to 7 respectively instead of using Compound Example 1 in Example 1, as shown in Table 3. Obtained toners were evaluated by the same evaluations as Example 1.

TABLE 3

| Example | Silicon Complex Compound |
|---|---|
| Example 1 | Compound Example 1 |
| Example 2 | Compound Example 2 |
| Example 3 | Compound Example 6 |
| Example 4 | Compound Example 27 |
| Example 5 | Compound Example 8 |
| Example 6 | Compound Example 13 |
| Example 7 | Compound Example 17 |

EXAMPLE 8

100 parts by weight of styrene-acrylate copolymer resin: CPR-600B which is available from Mitsui Chemicals, Inc., 5 parts by weight of color dye of yellow: C.I. pigment yellow 180, 3 parts by weight of low grade polypropylene: VISCOL 550-P which is available from Sanyo Chemical Industries, Ltd., 1 part by weight of the charge control agent comprising Compound Example 4, were treated by the similar procedure of Example 1, to prepare the yellow toner having 10 microns of the average particle size thereof and the developer. The obtained developer was evaluated by the similar procedure of Example 1. The measurement results thereof are shown in Table 4.

EXAMPLE 9

100 parts by weight of polyester resin: HP313 which is available from The Nippon Synthetic Chemical Industry Co., Ltd., 3 parts by weight of low grade polypropylene: VISCOL 550-P which is available from Sanyo Chemical Industries, Ltd., 6 parts by weight of carbon black: #44 which is available from Mitsubishi Chemical Corporation, 1 part by weight of the charge control agent comprising Compound Example 16, were treated by the similar procedure of Example 1 to prepare the black toner having 10 microns of the average particle size thereof and the developer. The obtained developer was evaluated by the similar procedure of Example 1. The measurement results thereof are shown in Table 4.

EXAMPLE 10

80 parts by weight of styrene monomer, 20 parts by weight of n-butyl acrylate monomer, 5 parts by weight of color dye of yellow: C.I. pigment yellow 180, 1.8 parts by weight of 2,2'-azoisobutyronitrile, 1 part by weight of the charge control agent comprising Compound Example 1, were pre-mixed homogeneously using a high speed mixer to obtain the monomer composition.

100 ml of 0.1 mol % sodium tertiary phosphate aqueous solution was diluted with 600 ml of distilled water. 18.7 ml of 1.0 mol/L calcium chloride aqueous solution was added thereto gradually with stirring, then 0.15 g of 20% of concentration of sodium dodecylbenzenesulfonate aqueous solution was added thereto to prepare dispersion liquid.

The dispersion liquid was added to the above monomer composition. It was heated until 65° C. with fast stirring using T.K. HOMO MIXER that is available from Tokushu Kika Kogyo Co., Ltd and then stirred for 30 minutes. Furthermore, it was heated until 80° C. with stirring at 100 rpm using a usual stirrer in turn, and then polymerization thereof was carried out at 80° C. for 6 hours.

After the polymerization, the reaction mixture was cooled, and the solid was filtered out. After the filtered solid was soaked into 5 weight % of concentration of hydrochloric acid aqueous solution in order to decompose calcium phosphate which was functioned as the dispersing agent, the solid was washed with water until its washing was neutral. It was dehydrated and dried to obtain the yellow toner having 10 microns of the average particle size thereof.

5 parts by weight of the obtained toner and 95 parts by weight of carrier of ferrite powder: F-150 which is available from Powder Tech Corporation were mixed to prepare the developer. The obtained developer was evaluated by the similar procedure of Example 1. The measurement results thereof are shown in Table 4.

EXAMPLE 11

80 parts by weight of styrene monomer, 20 parts by weight of n-butyl acrylate monomer, 5 parts by weight of carbon black: MA-100 which is available from Mitsubishi Chemical Corporation, 1.8 parts by weight of the 2,2'-azoisobutyronitrile, 1 part by weight of the charge control agent comprising Compound Example 20, were treated by the similar procedure of Example 10, to prepare the black toner having 13 microns of the average particle size thereof and the developer. The obtained developer was evaluated by the similar procedure of Example 1. The measurement results thereof are shown in Table 4.

EXAMPLE 12

100 parts by weight of styrene-acrylate copolymer: CPR-600B which is available from Mitsui Chemicals, Inc., 3 parts by weight of low grade polypropylene: VISCOL 550-P which is available from Sanyo Chemical Industries, Ltd., 5 parts by weight of color dye of magenta: C.I. Pigment Red 57:1, were pre-mixed homogeneously using a high speed mixer. It was kneaded with melting by an extruder. It was cooled, and granulated roughly by a vibration mill. The prepared rough granules were granulated finely using an air jet mill equipping with a classifier, to prepare the host particles of magenta toner having 10 microns of the particle size thereof.

1 part by weight of the guest particles of the charge control agent comprising Compound Example 10 was added externally to 108 parts by weight of the prepared host particles, to obtain the positive electrified toner for developing an electrostatic image.

5 parts by weight of the toner and 95 parts by weight of carrier of ferrite powder: F-150 which is available from Powder Tech Corporation were mixed to prepare the developer. The obtained developer was evaluated by the similar procedure of Example 1. The measurement results thereof are shown in Table 4.

EXAMPLE 13

100 parts by weight of stylene-acrylate copolymer: CPR-600B which is available from Mitsui Chemicals, Inc., 3 parts by weight of low grade polypropylene: VISCOL 550-P which is available from Sanyo Kasei Industries, Ltd., 5 parts by weight of oil soluble color dye of magenta: OIL PINK #312 which is available from Orient Chemical Industries, Ltd., 0.5 parts by weight of the charge control agent: BONTRON P-51 which is available from Orient Chemical Industries, Ltd., 0.5 parts by weight of the charge control agent: Compound Example 1, were treated by the similar procedure of Example 1, to prepare the magenta toner having 10 microns of the average particle size thereof and the developer. The obtained developer was evaluated by the similar procedure of Example 1. The measurement results thereof are shown in Table 4.

COMPARATIVE EXAMPLE 1

The silicon complex compound represented by the Compound Example c was synthesized using 2-naphthalenesulfate sodium salt instead of 1,5-naphthalenedisulfate disodium salt used for anion exchange in Synthetic Example 2, by using equimolar amounts of the silicon complex intermediate and the anion component. According to CHS elemental analysis of the silicon complex compound of the Compound Example c, the content of C in the compound was 72.94% (theoretical value: 72.99%), the content of H in the compound was 4.58% (theoretical value: 4.45%), and the content of S in the compound was 3.32% (theoretical value: 3.10%), and they were mostly identical with the theoretical values. Therefore, the obtained silicon complex compound is identified as the desired Compound Example c. Furthermore, the rate of weight-decrease of Compound Example c was 41.0%.

The toner was prepared by the similar procedure of Example 1 except that the silicon complex compound of Compound Example c represented by the following chemical formula was used instead of the silicon complex compound of Compound Example 1 used in the Example 1. The obtained toner was evaluated by the similar procedure of Example 1. The measurement results thereof are shown in Table 4.

Compound Example c

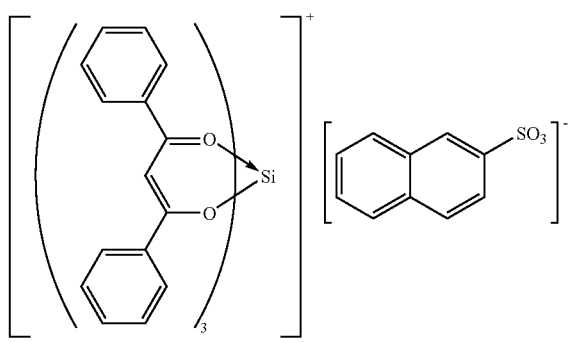

COMPARATIVE EXAMPLE 2

The toner was prepared by the similar procedure of Example 1 except that the silicon complex compound of Compound Example d represented by the following chemical formula was used instead of the silicon complex compound of Compound Example 1 used in the Example 1. The obtained toner was evaluated by the similar procedure of Example 1. The measurement results thereof are shown in Table 4.

Compound Example d

COMPARATIVE EXAMPLE 3

The positive electrified toner for developing an electrostatic image was prepared by the similar procedure of Example 1 except that the silicon complex intermediate of Compound Example a was used instead of the silicon complex compound of Compound Example 1 used in the Example 1. The obtained toner was evaluated by the similar procedure of Example 1.

COMPARATIVE EXAMPLE 4

The compound with incomplete anion-exchanging reaction was prepared by the similar procedure of Synthetic Example 1-2 except that the condition of the anion-exchanging reaction was changed as follows when the Compound Example 1 was synthesized.

28 g (33.7 mmol) of the silicon complex intermediate of Compound Example a was dispersed into water. 5.72 g (17.2 mmol) of 1,5-naphthalenedisulfate disodium salt was added thereto and dispersed for 24 hours at the room temperature. Obtained reactant was filtrated and washed with water until the electric conductivity of the filtrate lowered. It was dried at 80° C., to obtain 29.0 g of the charge control agent with incomplete anion-exchanging reaction, which mainly comprises the silicon complex compound of Compound Example 1. The content of allowable residual chlorine in the charge control agent was 0.36%.

The toner was prepared by the similar procedure of Example 1 except that the charge control agent with incomplete anion-exchanging reaction was used instead of the silicon complex compound of Compound Example 1 used in the Example 1. The obtained toner was evaluated by the similar procedure of Example 1. The measurement results thereof are shown in Table 4.

TABLE 4

| | | | | Property of Developer | | | | | |
| | | | | | Environmental Stability (Changing Rate of Quantity of Electrification (%)) | | | Property of Toner Image | | |
| Example No. | | Quantity of Initial Electrification (μC/g) | Electrification Stability | Low Temperature and low Humidity (5° C.: 30% RH) | High Temperature and High Humidity (35° C.: 90% RH) | Fogginess | Reproducibility of Fine Line | Electrification Stability and Durability | Phenomenon of Offset |
|---|---|---|---|---|---|---|---|---|---|
| Ex. | 1 | 59.5 | ○ | 2.9 | 3.7 | ○ | ○ | ○ | ○ |
| | 2 | 64.5 | ○ | 2.6 | 2.5 | ○ | ○ | ○ | ○ |
| | 3 | 59.5 | ○ | 3.0 | 3.9 | ○ | ○ | ○ | ○ |
| | 4 | 49.0 | ○ | 3.2 | 3.4 | ○ | ○ | ○ | ○ |
| | 5 | 66.9 | ○ | 2.7 | 3.6 | ○ | ○ | ○ | ○ |
| | 6 | 35.1 | ○ | 2.6 | 3.1 | ○ | ○ | ○ | ○ |
| | 7 | 26.1 | ○ | 3.1 | 3.4 | ○ | ○ | ○ | ○ |
| | 8 | 76.8 | ○ | 2.2 | 2.5 | ○ | ○ | ○ | ○ |
| | 9 | 22.1 | ○ | 2.3 | 3.2 | ○ | ○ | ○ | ○ |
| | 10 | 45.9 | ○ | 2.4 | 3.7 | ○ | ○ | ○ | ○ |
| | 11 | 24.5 | ○ | 4.9 | 4.9 | ○ | ○ | ○ | ○ |
| | 12 | 56.8 | ○ | 2.5 | 3.3 | ○ | ○ | ○ | ○ |
| | 13 | 49.5 | ○ | 3.4 | 4.4 | ○ | ○ | ○ | ○ |

TABLE 4-continued

| | | Property of Developer | | | | | Property of Toner Image | | |
|---|---|---|---|---|---|---|---|---|---|
| | | | | Environmental Stability (Changing Rate of Quantity of Electrification (%)) | | | | | |
| | | | | | High | | | | |
| Example No. | Quantity of Initial Electrification (µC/g) | Electri- fication Stability | Low Temperature and low Humidity (5° C.: 30% RH) | | Temperature and High Humidity (35° C.: 90% RH) | | Fogginess | Repro- ducibility of Fine Line | Electrification Stability and Durability | Phenomenon of Offset |
| Comp. 1 | 44.1 | ○ | 7.0 | Δ | 7.5 | Δ | ○ | ○ | X | ○ |
| Ex. 2 | 47.6 | ○ | 9.8 | Δ | 9.8 | Δ | ○ | ○ | X | ○ |
| 3 | 58.5 | ○ | 13.2 | X | 12.6 | X | ○ | ○ | X | ○ |
| 4 | 54.7 | ○ | 8.0 | Δ | 10.4 | X | ○ | ○ | X | ○ |

According to Table 4, it is obvious that the developers of Examples have excellent electrification stability, electrification durability and environmental stability. The toner images formed using the developers have no fogginess, excellent reproducibility of fine lines, excellent electrification stability and durability. Furthermore, the phenomenon of offset of the toner images is not observed. On the other hand, the developers of Comparative Examples have bad environmental stability, and are unsuitable for the use under the condition of high temperature and high humidity such as summer, or the condition of changing the temperature and the humidity.

INDUSTRIAL APPLICABILITY

The positive electrified charge control agent of the present invention is used for copying, for printing or for electrostatic powder paint by electro photographs of a copy machine, a printer or a facsimile. The positive electrified charge control agent is used by being added in the positive electrified toner for developing the electrostatic image, or in the powder paint.

The positive electrified toner for developing the electrostatic image comprising the positive electrified charge control agent is used for fixing the vivid images with no fogginess on the transfer-recording medium such as the paper and the film.

What is claimed is:

1. A positive electrified charge control agent comprising a silicon complex compound of an effective component represented by the following chemical formula (I) and/or chemical formula (II)

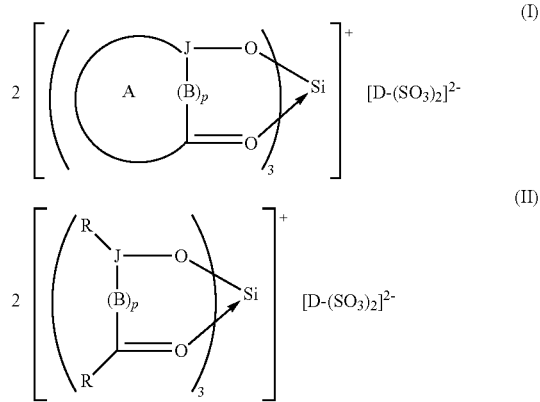

(in the formula (I) and formula (II), $[D-(SO_3)_2]^{2-}$ is a bivalent anion of an organic acid having at least two sulfonic acid groups, p is 0 or 1, B is a bonding line when p is 0, B is a carbon atom or a nitrogen atom when p is 1, J is a carbon atom or a nitrogen atom, A is an organic group which forms a ring with $(B)_p$ and J, both of R are same or different to each other and are an organic group, and these both of R are independent or form a heterocyclic ring).

2. The positive electrified charge control agent according to claim 1, wherein the group of

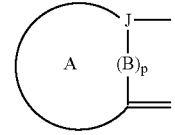

in the chemical formula (I) is represented by the following chemical formula (III)

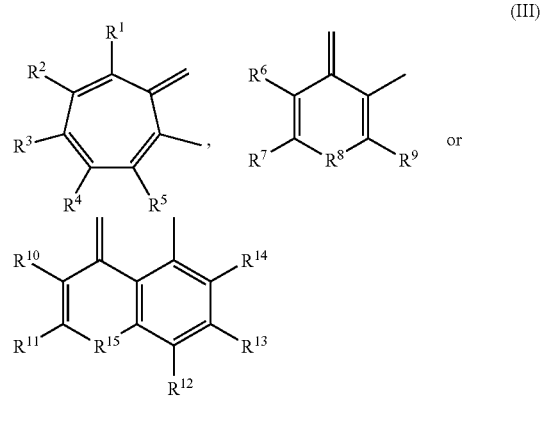

(in the chemical formula (III), $R^1$ to $R^7$ and $R^{10}$ to $R^{14}$ are same or different to each other and are selected from the group consisting of a hydrogen atom, a hydroxyl group, a hydroxyalkyl group, a carboxyl group, an alkoxycarbonyl group, a halogen atom, an alkyl group, an alkoxyl group, an acyl group, an alkenyl group, a nitro group, a cyano group, an amino group, an alicyclic group, an aralkyl group and an aryl group, or a group forming a saturated or unsaturated fused-ring of 3 to 7 carbons at positions of neighboring group; $R^8$ and $R^{15}$ are an oxygen atom, a carbonyl group, or an imino group; $R^9$ is selected from the group consisting of a hydrogen atom, a hydroxyl group, a hydroxyalkyl group, a carboxyl group, an alkoxycarbonyl group, a halogen atom, an alkyl group, an alkoxyl group, an acyl group, an alkenyl group, a nitro group, a cyano group, an amino group, an alicyclic group, an aralkyl group and an aryl group); and
the group of

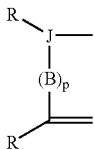

in the chemical formula (II) is represented by the following chemical formula (IV)

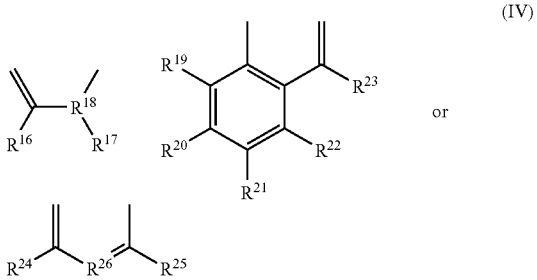

(IV)

or (in the chemical formula (IV), $R^{16}$, $R^{17}$ and $R^{23}$ to $R^{25}$ are same or different to each other and are selected from the group consisting of a hydrogen atom, a hydroxyl group, a hydroxyalkyl group, a carboxyl group, an alkoxycarbonyl group, a halogen atom, an alkyl group, an alkoxyl group, an acyl group, an alkenyl group, a nitro group, a cyano group, an amino group, an alicyclic group, an aralkyl group and an aryl group; $R^{18}$ is a methine or a nitrogen atom; $R^{19}$ to $R^{22}$ are same or different to each other and are selected from the group consisting of a hydrogen atom, a hydroxyl group, a hydroxyalkyl group, a carboxyl group, an alkoxycarbonyl group, a halogen atom, an alkyl group, an alkoxyl group, an acyl group, an alkenyl group, a nitro group, a cyano group, an amino group, an alicyclic group, an aralkyl group and an aryl group, or a group forming a saturated or unsaturated fused-ring of 3 to 7 carbons at positions of neighboring group; $R^{26}$ is a nitrogen atom or a carbon atom having one or more substitutional groups or no substitutional group).

3. The positive electrified charge control agent according to claim 1, wherein said silicon complex compound represented by the chemical formula (I) is a compound obtained by an ion-exchanging reaction of a silicon complex salt represented by the following chemical formula (V)

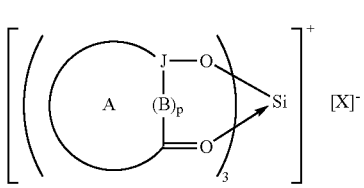

(V)

(in the chemical formula (V), X is a halogen atom; p, B, J and A are the same above) with an organic acid or a salt thereof; and said silicon complex compound represented by the chemical formula (II) is a compound obtained by an ion-exchanging reaction of a silicon complex salt represented by the following chemical formula (VI)

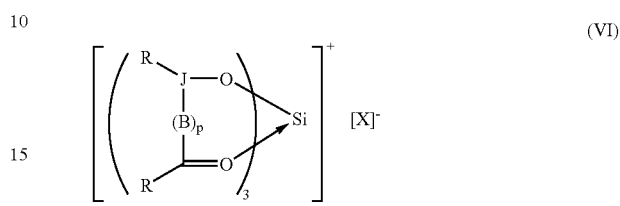

(VI)

(in the chemical formula (VI), X is a halogen atom; p, B, J and R are the same above) with an organic acid or a salt thereof.

4. The positive electrified charge control agent according to claim 1, wherein a content of allowable residual halogen in the silicon complex compound represented by the chemical formula (I) or the chemical formula (II) is at most 0.2%.

5. The positive electrified charge control agent according to claim 1, wherein a rate of weight-decrease of the silicon complex compound represented by the chemical formula (I) or the chemical formula (II) after heating for 2 hours under 180° C. is at most 10.0%.

6. The positive electrified charge control agent according to claim 1, wherein a volume resistivity of the silicon complex compound represented by the chemical formula (I) or the chemical formula (II) is $1.0 \times 10^{13}$ to $5.0 \times 10^{15} \Omega \cdot cm$.

7. A positive electrified toner for developing an electrostatic image comprising a positive electrified charge control agent including a silicon complex compound of an effective component represented by the following chemical formula (I) and/or chemical formula (II)

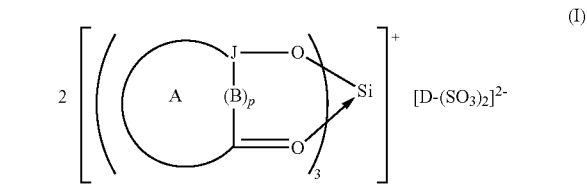

(I)

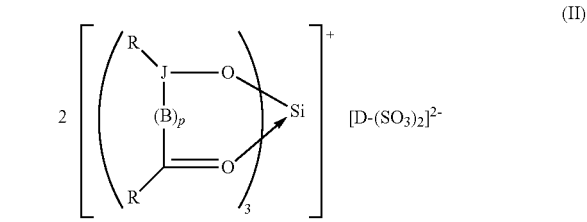

(II)

(in the formula (I) and formula (II), $[D\text{-}(SO_3)_2]^{2-}$ is a bivalent anion of an organic acid having at least two sulfonic acid groups, p is 0 or 1, B is a bonding line when p is 0, B is a carbon atom or a nitrogen atom when p is 1, J is a carbon atom or a nitrogen atom, A is an organic group which forms a ring with $(B)_p$ and J, both of R are same or different to each other and are an organic group, and these both of R are independent or form a heterocyclic ring).

8. The positive electrified toner for developing the electrostatic image according to claim 7, wherein the group of

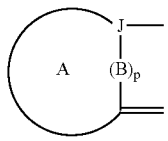

in the chemical formula (I) is represented by the following chemical formula (III)

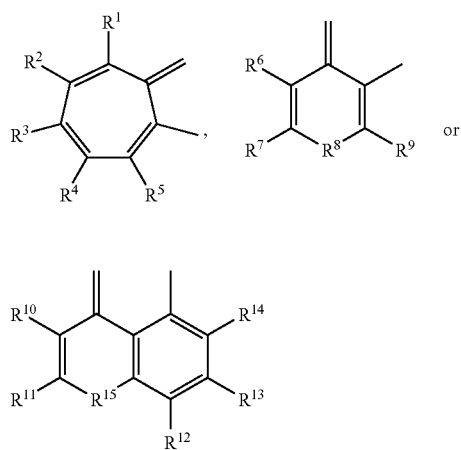

(III)

(in the chemical formula (III), $R^1$ to $R^7$ and $R^{10}$ to $R^{14}$ are same or different to each other and are selected from the group consisting of a hydrogen atom, a hydroxyl group, a hydroxyalkyl group, a carboxyl group, an alkoxycarbonyl group, a halogen atom, an alkyl group, an alkoxyl group, an acyl group, an alkenyl group, a nitro group, a cyano group, an amino group, an alicyclic group, an aralkyl group and an aryl group, or a group forming a saturated or unsaturated fused-ring of 3 to 7 carbons at positions of neighboring group; $R^8$ and $R^{15}$ are an oxygen atom, a carbonyl group, or an imino group; $R^9$ is selected from the group consisting of a hydrogen atom, a hydroxyl group, a hydroxyalkyl group, a carboxyl group, an alkoxycarbonyl group, a halogen atom, an alkyl group, an alkoxyl group, an acyl group, an alkenyl group, a nitro group, a cyano group, an amino group, an alicyclic group, an aralkyl group and an aryl group); and the group of

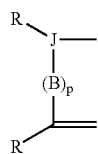

in the chemical formula (II) is represented by the following chemical formula (IV)

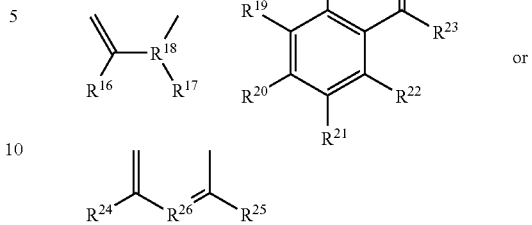

(IV)

or (in the chemical formula (IV), $R^{16}$, $R^{17}$ and $R^{23}$ to $R^{25}$ are same or different to each other and are selected from the group consisting of a hydrogen atom, a hydroxyl group, a hydroxyalkyl group, a carboxyl group, an alkoxycarbonyl group, a halogen atom, an alkyl group, an alkoxyl group, an acyl group, an alkenyl group, a nitro group, a cyano group, an amino group, an alicyclic group, an aralkyl group and an aryl group; $R^{18}$ is a methine or a nitrogen atom; $R^{19}$ to $R^{22}$ are same or different to each other and are selected from the group consisting of a hydrogen atom, a hydroxyl group, a hydroxyalkyl group, a carboxyl group, an alkoxycarbonyl group, a halogen atom, an alkyl group, an alkoxyl group, an acyl group, an alkenyl group, a nitro group, a cyano group, an amino group, an alicyclic group, an aralkyl group and an aryl group, or a group forming a saturated or unsaturated fused-ring of 3 to 7 carbons at positions of neighboring group; $R^{26}$ is a nitrogen atom or a carbon atom having one or more substitutional groups or no substitutional group).

9. The positive electrified toner for developing the electrostatic image according to claim 7, wherein said silicon complex compound represented by the chemical formula (I) is a compound obtained by an ion-exchanging reaction of a silicon complex salt represented by the following chemical formula (V)

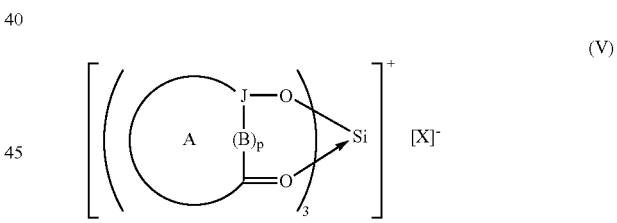

(V)

(in the chemical formula (V), X is a halogen atom; p, B, J and A are the same above) with an organic acid or a salt thereof; and said silicon complex compound represented by the chemical formula (II) is a compound obtained by an ion-exchanging reaction of a silicon complex salt represented by the following chemical formula (VI)

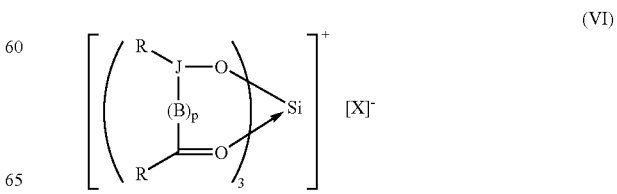

(VI)

(in the chemical formula (VI), X is a halogen atom; p, B, J and R are the same above) with an organic acid or a salt thereof.

10. The positive electrified toner for developing the electrostatic image according to claim 7, wherein a content of allowable residual halogen in the silicon complex compound represented by the chemical formula (I) or the chemical formula (II) is at most 0.2%.

11. The positive electrified toner for developing the electrostatic image according to claim 7, wherein a rate of weight-decrease of the silicon complex compound represented by the chemical formula (I) or the chemical formula (II) after heating for 2 hours under 180° C. is at most 10.0%.

12. The positive electrified toner for developing the electrostatic image according to claim 7, wherein a volume resistivity of the silicon complex compound represented by the chemical formula (I) or the chemical formula (II) is $1.0 \times 10^{13}$ to $5.0 \times 10^{15}$ Ω·cm.

13. The positive electrified toner for developing the electrostatic image according to claim 7, wherein 0.1 to 10 parts by weight of the positive electrified charge control agent and 100 parts by weight of a resin for the toner are included.

14. A charge control method of a positive electrified toner for developing an electrostatic image comprising a step for making the toner positively electrified by friction, wherein the toner includes a component of a positive electrified charge control agent comprising a silicon complex compound of an effective component represented by the following chemical formula (I) and/or chemical formula (II)

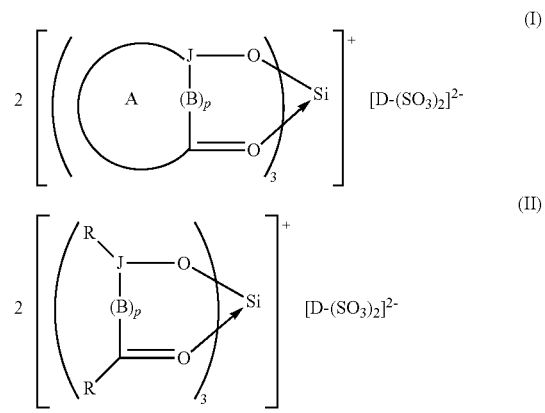

(in the formula (I) and formula (II), $[D\text{-}(SO_3)_2]^{2-}$ is a bivalent anion of an organic acid having at least two sulfonic acid groups, p is 0 or 1, B is a bonding line when p is 0, B is a carbon atom or a nitrogen atom when p is 1, J is a carbon atom or a nitrogen atom, A is an organic group which forms a ring with $(B)_p$ and J, both of R are same or different to each other and are an organic group, and these both of R are independent or form a heterocyclic ring).

* * * * *